United States Patent
Wang et al.

(10) Patent No.: US 11,193,155 B2
(45) Date of Patent: Dec. 7, 2021

(54) DESIGNER α 6-FUCOSIDASE MUTANTS ENABLE DIRECT CORE FUCOSYLATION OF INTACT N-GLYCOPEPTIDES AND N-GLYCOPROTEINS

(71) Applicant: UNIVERSITY OF MARYLAND, COLLEGE PARK, College Park, MD (US)

(72) Inventors: Lai-Xi Wang, Ellicott City, MD (US); Chao Li, College Park, MD (US); Shilei Zhu, Halethorpe, MD (US)

(73) Assignee: UNIVERSITY OF MARYLAND, COLLEGE PARK, College Park, MD (US)

( * ) Notice: Subject to any disclaimer, the term of this patent is extended or adjusted under 35 U.S.C. 154(b) by 0 days.

(21) Appl. No.: 16/323,355

(22) PCT Filed: Aug. 10, 2017

(86) PCT No.: PCT/US2017/046232
§ 371 (c)(1),
(2) Date: Feb. 5, 2019

(87) PCT Pub. No.: WO2018/031734
PCT Pub. Date: Feb. 15, 2018

(65) Prior Publication Data
US 2019/0185898 A1    Jun. 20, 2019

Related U.S. Application Data

(60) Provisional application No. 62/373,151, filed on Aug. 10, 2016.

(51) Int. Cl.
*C12N 9/24* (2006.01)
*C12P 21/00* (2006.01)

(52) U.S. Cl.
CPC .......... *C12P 21/005* (2013.01); *C12N 9/2402* (2013.01); *C12Y 302/01127* (2013.01); *C07K 2319/21* (2013.01); *C07K 2319/50* (2013.01)

(58) Field of Classification Search
CPC .................... C12N 9/24; C12N 9/2402; C12Y 302/01127; C12P 21/005; C12K 2317/41
See application file for complete search history.

(56) References Cited

U.S. PATENT DOCUMENTS

| | | |
|---|---|---|
| 7,524,821 B2 | 4/2009 | Wang et al. |
| 7,556,809 B2 | 7/2009 | Wang |
| 7,604,804 B2 | 10/2009 | Wang et al. |
| 7,728,106 B2 | 6/2010 | Wang |
| 7,807,405 B2 | 10/2010 | Wang |
| 8,354,247 B2 | 1/2013 | Wang |
| 8,900,826 B2 | 12/2014 | Wang |
| 9,175,326 B2 | 11/2015 | Wang |
| 9,434,786 B2 | 9/2016 | Wang et al. |
| 9,605,050 B2 | 3/2017 | Wang |
| 9,845,360 B2 | 12/2017 | Wang et al. |
| 9,850,473 B2 | 12/2017 | Wang |
| 2015/0087814 A1 | 3/2015 | Wang et al. |
| 2015/0176045 A1 | 6/2015 | Marcel et al. |
| 2019/0002542 A1 | 1/2019 | Wang et al. |
| 2019/0002945 A1 | 1/2019 | Wang et al. |

FOREIGN PATENT DOCUMENTS

WO    WO2015057066 A1    4/2015

OTHER PUBLICATIONS

Klontz et al. 2020; Structure and dynamics of an a-fucosidase reveal a mechanism for highly efficient IgG transfucosylation. Nature Communications.II:6204, pp. 1-14.*
Li et al. 2017; Designer a-1,6-fucosidasemutants enable direct core fucosylation of intact N-glycopeptides and N-glcyoproteins. Journal of the American Chemical Society. 139:15074-15087.*
Osanjo et al. 2007; Directed evolution of -L-fucosidase from Thermotoga maritima into a -L-transfucosidase. Biochemistry. 46: 1022-1033.*
Saumonneau et al. 2016, published Nov. 17, 2015; Design of an -L-transfucosidase for the synthesis of fucosylated HMOs. Glycobiology. 28(3): 261-269.*
Amin, M. N. et al. Convergent Synthesis of Homogenous $Glc_1Man_9GLcNAc_2$-Protein and Derivatives as Ligands of Molecular Chaperones in Protein Quality Control, *J. Am. Chem. Soc.* (2011), 133:14404-14417.
Andre, S. et al. Substitutions in the N-Glycan Core as Regukators of Biorecognition: The Case of Core-Fucose and Bisecting GlcNAc Moities, *Biochemistry* (2007), 46:6984-6995.
Andre, S. et al. From structural to functional glycomics: core substitutions as molecular switches for shape and lectin affinity of N-glycans; *Biol. Chem.* (2009), 390: 557-565.
Ashida, H. et al. Two Distinct α-L-Fucosidases from Bifidobacterium bifidum are essential for the utilization of fucosylated milk oligosaccharides and glycoconjugates, *Glycobiology* (2009), 19:1010-1017.
Becerra, J. E. et al. Preparative scale purification of fucosyl-N-acetylglucosamine disaccharides and their evaluation as potential prebiotics and antiadhesins, *Appl. Microbiol. Biotechnol.* (2015), 99:7165-7176.

(Continued)

*Primary Examiner* — Karen Cochrane Carlson
(74) *Attorney, Agent, or Firm* — Marianne Fuierer; Olive Law Group, PLLC

(57) ABSTRACT

The present invention provides for novel fucosidase mutants that server as fuco-ligases for core fucosylation of a range of biological glycopeptides and glycoproteins including intact therapeutic antibodies. Several mutants with mutation at the general acid/base residue E274 of the *Lactobacillus casei* α1,6-fucosidase, including E274A, E274S, and E274G, were able to efficiently fucosylate a wide variety of complex N-glycopeptides and intact glycoproteins. The site specific mutants enable the transfer of fucose to a core GlcNAc-Asn residue and useful for drug delivery and vaccine development.

11 Claims, 23 Drawing Sheets
Specification includes a Sequence Listing.

(56) References Cited

OTHER PUBLICATIONS

Brzezicka, K. et al. Synthesis and Microarray-Assisted Binding Studies of Core Xylose and Fucose Containing N-Glycans, *ACS Chem. Biol.* (2015), 10:1290-1302.

Calderon, A. D. et al. Substrate specificity of FUT8 and chemoenzymatic synthesis of core-fucosylated asymmetric N-glucans, *Org. Biomol. Chem.* (2016), 14:4027-4031.

Chen, C. Y. et al. Fucosyltransferase 8 as a functional regulator of nonsmall cell lung cancer, *Proc. Natl. Acad. Sci. USA* (2013), 110:630-635.

Cobucci-Ponzano, B. et al. Glycosynthases as tools for the production of glycan analogs of natural products, *Nat. Prod. Rep.* (2012), 29:697-709.

Cobucci-Ponzano, B. et al. β-Glycosyl Azides as Substrates for α-Glycosynthases: Preparation of Efficient α-L-Fucosynthases, *Chem. Biol.* (2009), 16:1097-1108.

Cobucci-Ponzano, B. et al. Exploitation of β-glycosyl azides for the preparation of α-glycosynthases, *Biocatalysis and Biotransformation* (2012), 30:288-295.

Cobucci-Ponzano, B. et al. A novel α-D-galactosynthase from *Thermotoga maritima* converts β-D-galactopyranosyl azide to α-galactooligosaccharides, *Glycobiology* (2011), 21:448-456.

Danby, P. M. et al. Advances in Enzymatic Glycoside Synthesis, *ACS Chem. Biol.* (2016), 11:1784-1794.

Dube, D. H. et al. Glycans in Cancer and Inflammation—Potential for Therapeutics and Diagnostics, *Nat. Rev. Drug Discov.* (2005), 4:477-488.

Dwek, R. A. Glycobiology: Towards Understanding the Function of Sugars, *Chem. Rev.* (1996), 96:683-720.

Giddens, J. P. et al. Endo-F3 Glycosynthase Mutants Enable Chemoenzymatic Synthesis of Core-fucosylated Triantennary Complex Type Glycopeptides and Glycoproteins. *J. Biol. Chem.* (2016) 291:9356-9370.

Haltiwanger, R. S. et al. Role of Glycosylation in Development, *Annu. Rev. Biochem.* (2004), 73:491-537.

Hancock, S. M. et al. Engineering of glycosidases and glycosyltransferases, *Curr. Opin. Chem. Biol.* (2006), 10:509-519.

Hart, G. W. et al. Glycomics hits the big time, *Cell* (2010), 143:672-676.

Helenius, A. et al. Intracellular Functions of N-Linked Glycans, *Science* (2001), 291:2364-2369.

Huang, W. et al. Chemoenzymatic glycoengineering of intact IgG antibodies for gain of functions. *J. Am. Chem. Soc.* (2012) 134:12308-12318.

Huang, W. et al. Unusual Transglycosylation Activity of *Flavobacerium meningosepticum* Endoglycosidases Enables Convergent Chemoenzymatic Synthesis of Core Fucosylated Complex N-Glycopeptides, *ChemBioChem* (2011) 12:932-941.

Huang, W. et al. Arthrobacter endobeta-N-acetylglucosaminidase shows transglycosylation activity on complex-type N-glycan oxazolines: one-pot conversion of ribonuclease B to sialylated ribonuclease C. *ChemBioChem* (2010) 11:1350-1355.

Jahn, M. et al. Thioglycoligases: Mutant Glycosidases for Thioglycoside Synthesis, *Angew. Chem. Int. Ed.* (2003), 42:352-354.

Jefferis, R. Glycosylation as a strategy to improve antibody-based therapeutics. *Nat. Rev.Drug Discov.* (2009) 8:226-234.

Kamoda, S. et al. Rapid and Sensitive Screening of N-Glycans as 9-Fluorenylmethyl Derivatives by High-Performance Liquid Chromatography: A Method Which Can Recover Free Oligosaccharides after Analysis, *J. Proteome Res.* (2005), 4:146-152.

Kiessling, L. L. et al. Chemical Approaches to Glycobiology, *Annu. Rev. Biochem.* (2010), 79:619-653.

Kim, Y. W. et al. O-Glycoligases, a new category of glycoside bond-forming mutant glycosidases, catalyse facile syntheses of isoprimeverosides, *Chem. Commun. (Camb)* (2010), 46:8725-8727.

Lai, J. I. et al. Divergent Antibody Subclass and Specificity Profiles but Not Protective HLA-B Alleles are Associated with Variable Antibody Effector Function among HIV-1 Controllers, *J. Virol.* (2014), 88:2799-2809.

Lee, S. H. et al. Loss of Core Fucosylation of Low-Density Lipoprotein Receptor-Related Protein-1 Impairs Its Function, Leading to the Upregulation of Serum Levels of Insulin-Like Growth Factor-Binding Protein 3 in Fut8$^{-/-}$ Mice, *J. Biochem.* (2006), 139:391-398.

Li, T. et al. Modulating IgG effector function by Fc glycan engineering, *Proc. Natl. Acad. Sci. USA* (2017), 114:3485-3490.

Li, C. et al. Transglycosylation of engineered cyclodextrin glucanotransferases as O-glycoligases, *Carbohydr. Polym.* (2014), 99:39-46.

Li, W. et al. Core Fucosylation of IgG B Cell Receptor is Required for Antigen Recognition and Antibody Production, *J. Immunol.* (2015), 194:2596-2606.

Li, L. et al. Efficient chemoenzymatic synthesis of an N-glycan isomer library, *Chem. Sci.* (2015), 6:5652-5661.

Li, T. et al. Glycosynthase mutants of endoglycosidase S2 show potent transglycosylation activity and remarkably relaxed substrate specificity for antibody glycosylation remodeling, *Journal of Biological Chemistry*, (2016) 291(32):16508-16518.

Lin, H. et al. Blocking core fucosylation of TGF-β1 receptors downregulates their functions and attenuates the epithelial-mesenchymal transition of renal tubular cells, *Am. J. Physiol. Renal. Physiol.* (2011), 300:F1017-F1025.

Liu, S. W. et al. Identification of Essential Residues of Human α-L-Fucosidase and Tests of Its Mechanism, *Biochemistry* (2009), 48:110-120.

Lomino, J.V. et al. Triggered *Mycobacterium tuberculosis* Heparin-Binding Hemagglutinin, *J. Bacteriol.* (2011), 193:2089-2096.

Mackenzie, L. F. et al. Glycosynthases: Mutant Glycosidases for Oligosaccharide Synthesis, *J. Am. Chem. Soc.* (1998), 120:5583-5584.

Malet, C. et al. From β-glucanase to β-glucansynthase: glycol transfer to α-glycosyl fluorides catalyzed by a mutant endoglucanase lacking its catalytic nucleophile, *FEBS Lett.* (1998), 440:208-212.

Mimura, Y. Glycosylation engineering of therapeutic IgG antibodies: challenges for the safety, functionality and efficacy, *Protein Cell* (2018) 9:47-62.

Moracci, M. et al. Restoration of the Activity of Active-Site Mutants of the Hyperthermophilic β-Glycosidase from *Sulfolobus solfataricus*: Dependence of the Mechanism on the Action of External Nucleophiles, *Biochemistry* (1998), 37:17262-17270.

Nagorny, P. et al. Toward Fully Synthetic Homogeneous β-Human Follicle-Stimulating Hormone (β-hFSH) with a Biantennary N-Linked Dodecasaccaride. Synthesis of β-hFSH with Chitobiose Units at the Natural Linkage Sites, *J. Am. Chem. Soc.* (2009), 131:5792.

Nakano, M. et al. Site-specific analysis of N-glycans on haptoglobin in sera of patients with pancreatic cancer: A novel approach for the development of tumor markers, *Int. J. Cancer* (2008), 122:2301-2309.

Nimmerjahn, F. et al. FCγ receptors as regulators of immune responses, *Nat. Rev. Immunol.* (2008), 8:34-47.

Pinho, S. S. et al. Glycosylation in cancer: mechanisms and clinical implications, *Nat. Rev. Cancer* (2015), 15:540-555.

Petrescu, A. J. et al. Structural aspects of glycomes with a focus on N-glycosylation and glycoprotein folding, *Curr. Opin. Struct. Biol.* (2006), 16:600-607.

Pinho, S. S. et al. Modulation of E-cadherin function and dysfunction by N-glycosylation, *Cell. Mol. Life Sci.* (2011), 68:1011-1020.

Perugino, G. et al. Oligosaccharide synthesis by glycosynthases, *Trends Biotechnol.* (2004), 22:31-37.

Rillahan, C. D. Glycan Microarrays for Decoding the Glycome, *Annu. Rev. Biochem.* (2011), 80:797-823.

Rodriguez-Diaz, J. et al. Utilization of natural fucosylated oligosaccharides by three novel alpha-L-fucosidases from a probiotic *Lactobacillus casei* strain. *Appl. Environ. Microbiol.* (2011) 77:703-705.

Rodriguez-Diaz, J. et al. Syntheis of Fucosyl-N-Acetylglucosamine Disaccharides by Transfucosylation Using α-L-Fucosidases from *Lactobacillus casei*, *Appl. Environ. Microbiol.* (2013), 79:3847-3850.

Sakurama, H. et al. 1,3-1,4-α-L-Fucosynthase That Specifically Introduces Lewis a/x Antigens into Type-1/2 Chains, *J. Biol. Chem.* (2012), 287:16709-16719.

(56) References Cited

OTHER PUBLICATIONS

Sakurama, H. et al. Differences in the Substrate Specificities and Active-Site Structures of Two α-L-Fucosidases (Glycoside Hydrolaes Family 29) from *Bacteroides thetaiotaomicron*, *Biosci. Biotechnol. Biochem.* (2012), 76:1022-1024.

Sato, Y. et al. Early Recognition of Hepatocellular Carcinoma based on Altered Profiles of Alpha-Fetoprotein, *N. Engl. J. Med.* (1993), 328:1802-1806.

Schmaltz, R. M. et al. Enzymes in the Synthesis of Glycoconjugates, *Chem. Rev.* (2011), 111:4259-4307.

Shaikh, F. A. et al. Identifying the Catalytic Acid/Base in GH29 α-L-Fucosidase Subfamilies, *Biochemistry* (2013), 52:5857-5864.

Shaikh F. A. et al. Teaching old enzymes new tricks: engineering and evolution of glycosidases and glycol transferases for improved glycoside synthesis, *Biochem. Cell Biol.* (2008), 86:169-177.

Shen, A. et al. Simplified, enhanced protein purification using an inducible, autoprocessing enzyme tag. *PloS One* (2009) 4:e8119.

Sugiyama, Y. et al. Introduction of H-antigens into oligosaccharides and sugar chains of glycoproteins using highly efficient 1,2-α-L-fucosynthase, *Glycobiology* (2016), 26:1235-1247.

Sugiyama , Y. et al. Application study of 1,2-α-l-fucosynthase: introduction of Fucα1-2Gal disaccharide structures of N-glycan, ganglioside, and xyloglucan oligosaccharide, *Biotechnol. Biochem.* (2017), 81:283-291.

Sulzenbacher, G. et al. Crystal Structure of Thermotoga maritima α-L-Fucosidase, *J. Biol. Chem.* (2004), 279:13119-13128.

Sun, B. et al. Pre-Activation-Based One-Pot Synthesis of an α-(2,3)-Sialylated Core-Fucosylated Complex Type Bi-Antennary N-Glycan Dodecasaccharide, *Chem. Eur. J.* (2008), 14:7072-7081.

Taniguchi, N. et al. Chapter Two—Glycans and Cancer: Role of N-Glycans in Cancer Biomarker, Progression and Metastasis, and Therapeutics, *Adv. Cancer Res.* (2015) 126:11-51.

Tseng, T. H. et al. Substrate Preference and Interplay of Fucosyltransferase 8 and N-Acetylglucosaminyltransferases, *J. Am. Chem. Soc.* (2017), 139:9431-9434.

Varki, A. Biological roles of oligosaccharides: all of the theories were correct, *Glycobiology* (1993), 3:97-130.

Venkatachalam, M. A. et al. New wrinkles in old receptors: core fucosylation is yet another target to inhibit TGF-β signaling, *Kidney Int.* (2013), 84:11-14.

Voynow, J. A. et al. Purification and Characterization of GDP-L-fucose-N-acetyl β-D-glucosamine α1→6Fucosyltransferase from Cultured Human Skin Fibroblasts, *J. Biol. Chem.* (1991), 266:21572-21577.

Wada, J. et al. 1,2-α-L-Fucosynthase: A glycosynthase derived from an inverting α-glycosidase with an unusual reaction mechanism, *FEBS Lett.* (2008), 582:3739-3743.

Wang, L. X. et al. Chemoenzymatic Synthesis of HIV-1 gp41 Glycopeptides: Effects of Glycosylation on the Anti-HIV Activity and α-Helix Bundle-Forming Ability of Peptide C34, *ChemBioChem* (2005), 6:1068-1074.

Wang, L. X. et al. Chemical and chemoenzymatic synthesis of glycoproteins for deciphering functions. *Chem. Biol.* (2014) 21:51-66.

Wang, X. et al. Dysregulation of TGF-β1 receptor activation leads to abnormal lung development and emphysema-like phenotype in core fucose-deficient mice, *Proc. Natl. Acad. Sci. USA* (2005), 102:15791-15796.

Wang, X. et al. Core Fucosylation Regulates Epidermal Growth Factor Receptor-mediated Intracellular Signalling, *J. Biol. Chem.* (2006), 281:2572-2577.

Wang, L. X. Expanding the Repertoire of Glycosynthases, *Chem. Biol.* (2009), 16:1026-1027.

Williams, S. J. et al. Glycosyl fluorides in enzymatic reactions, *Carbohydr. Res.* (2000), 327:27-46.

Yang, Q. et al. Revisiting the substrate specificity of mammalian α1,6-fucosyltransferase reveals that it catalyzes core fucosylation of N-glycans lacking α1,3-arm GlcNAc, *J. Biol. Chem.* (2017) doi: 10.1074/jbc.M117.804070.

Yang, Q. et al. Mammalian α-1,6-Fucosyltransferase (FUT8) is the Sole Enzyme Responsible for the N-Acetylglucosaminyltranferase I-independent Core Fucosylation of High-mannose N-Glycans, *J. Biol. Chem.* (2016), 291:11064-11071.

\* cited by examiner

A

B

SEQUENCE LISTING

<160> NUMBER OF SEQ ID NOS: 31

<210> SEQ ID NO 1
<211> LENGTH: 345
<212> TYPE: PRT
<213> ORGANISM: Artificial Sequence
<220> FEATURE:
<223> OTHER INFORMATION: Synthetic Construct

<400> SEQUENCE: 1

```
Met Asn Asp Asn Val Ala Trp Phe Lys Gln Ala Lys Tyr Gly Met Met
1               5                   10                  15

Ile His Trp Gly Leu Tyr Ser Leu Leu Ala Gly Glu Tyr Arg Gly Glu
            20                  25                  30

Ser Ser Ser Ala Tyr Ala Glu Trp Ile Gln Ser Lys Phe Gln Ile Pro
        35                  40                  45

Asn Ala Glu Tyr Gly Asn Leu Ala Thr Ala Phe Asn Pro Leu Tyr Phe
    50                  55                  60

Asp Ala Lys Lys Ile Val Ala Leu Ala Lys Gln Cys Gly Met Gln Tyr
65                  70                  75                  80

Leu Val Val Thr Thr Lys His His Asp Gly Phe Ala Met Tyr His Ser
                85                  90                  95

Lys Val Asp Ala Tyr Asn Val Tyr Asp Ala Thr Pro Phe His Arg Asp
            100                 105                 110

Ile Ile Gly Glu Leu Ala Glu Ala Cys Gln Lys Ala Gly Leu Lys Phe
        115                 120                 125

Gly Leu Tyr Tyr Ser Gln Asp Leu Asp Trp His Asp Pro Asn Gly Gly
    130                 135                 140

Gly Tyr Lys Ser Asn Asp Val Glu Thr Ala Gly Thr Thr Trp Asp Asn
145                 150                 155                 160

Ser Trp Asp Phe Pro Asp Glu Asp Gln Lys Asn Phe Asp Leu Cys Phe
                165                 170                 175

Asp Asn Lys Ile Leu Pro Gln Ile Lys Glu Ile Met Ser Asn Tyr Gly
            180                 185                 190

Asp Ile Ala Thr Ala Trp Phe Asp Val Pro Met Thr Leu Ser Glu Ala
        195                 200                 205

Gln Ser Gln Thr Ile Tyr Asp Thr Val Arg Glu Leu Gln Pro Asn Cys
    210                 215                 220

Leu Ile Asn Ser Arg Leu Gly Asn Gly Lys Tyr Asp Phe Val Ser Leu
225                 230                 235                 240

Gly Asp Asn Glu Ile Pro Lys Asn Lys Glu Asp Met Asn Lys Thr Asp
                245                 250                 255

Val Asp Tyr Asn Glu Ile Thr Gly Phe Lys Pro Ser Pro Leu Gly Leu
            260                 265                 270

Tyr Ala Thr Ala Gly Thr Ile Asn Asp Ser Trp Gly Phe Ser Tyr His
```

```
                    275                 280                 285
Asp Gln Asn Trp Lys Thr Pro Arg Thr Leu Tyr Arg Tyr Lys Gln His
            290                 295                 300
Leu Asn Asp Phe Gly Ile Asn Tyr Leu Leu Asn Val Gly Leu Asp Pro
305                 310                 315                 320
Leu Gly Arg Val Pro Met Met Ala Glu Glu Asn Leu Leu Ala Ala Lys
                325                 330                 335
Ala Leu Glu Asp Glu Ala Asn Arg Leu
            340                 345

<210> SEQ ID NO 2
<211> LENGTH: 345
<212> TYPE: PRT
<213> ORGANISM: Artificial Sequence
<220> FEATURE:
<223> OTHER INFORMATION: Synthetic Construct

<400> SEQUENCE: 2

Met Asn Asp Asn Val Ala Trp Phe Lys Gln Ala Lys Tyr Gly Met Met
1               5                   10                  15
Ile His Trp Gly Leu Tyr Ser Leu Leu Ala Gly Glu Tyr Arg Gly Glu
            20                  25                  30
Ser Ser Ser Ala Tyr Ala Glu Trp Ile Gln Ser Lys Phe Gln Ile Pro
        35                  40                  45
Asn Ala Glu Tyr Gly Asn Leu Ala Thr Ala Phe Asn Pro Leu Tyr Phe
    50                  55                  60
Asp Ala Lys Lys Ile Val Ala Leu Ala Lys Gln Cys Gly Met Gln Tyr
65                  70                  75                  80
Leu Val Val Thr Thr Lys His His Asp Gly Phe Ala Met Tyr His Ser
                85                  90                  95
Lys Val Asp Ala Tyr Asn Val Tyr Asp Ala Thr Pro Phe His Arg Asp
            100                 105                 110
Ile Ile Gly Glu Leu Ala Glu Ala Cys Gln Lys Ala Gly Leu Lys Phe
        115                 120                 125
Gly Leu Tyr Tyr Ser Gln Asp Leu Asp Trp His Asp Pro Asn Gly Gly
    130                 135                 140
Gly Tyr Lys Ser Asn Asp Val Glu Thr Ala Gly Thr Thr Trp Asp Asn
145                 150                 155                 160
Ser Trp Asp Phe Pro Asp Glu Asp Gln Lys Asn Phe Asp Leu Cys Phe
                165                 170                 175
Asp Asn Lys Ile Leu Pro Gln Ile Lys Glu Ile Met Ser Asn Tyr Gly
            180                 185                 190
Asp Ile Ala Thr Ala Trp Phe Asp Val Pro Met Thr Leu Ser Glu Ala
        195                 200                 205
Gln Ser Gln Thr Ile Tyr Asp Thr Val Arg Glu Leu Gln Pro Asn Cys
    210                 215                 220
Leu Ile Asn Ser Arg Leu Gly Asn Gly Lys Tyr Asp Phe Val Ser Leu
225                 230                 235                 240
Gly Asp Asn Glu Ile Pro Lys Asn Lys Glu Asp Met Asn Lys Thr Asp
                245                 250                 255
Val Asp Tyr Asn Glu Ile Thr Gly Phe Lys Pro Ser Pro Leu Gly Leu
            260                 265                 270
Tyr Ser Thr Ala Gly Thr Ile Asn Asp Ser Trp Gly Phe Ser Tyr His
        275                 280                 285
Asp Gln Asn Trp Lys Thr Pro Arg Thr Leu Tyr Arg Tyr Lys Gln His
```

```
                290                 295                 300

Leu Asn Asp Phe Gly Ile Asn Tyr Leu Leu Asn Val Gly Leu Asp Pro
305                 310                 315                 320

Leu Gly Arg Val Pro Met Met Ala Glu Glu Asn Leu Leu Ala Ala Lys
                325                 330                 335

Ala Leu Glu Asp Glu Ala Asn Arg Leu
                340                 345

<210> SEQ ID NO 3
<211> LENGTH: 345
<212> TYPE: PRT
<213> ORGANISM: Artificial Sequence
<220> FEATURE:
<223> OTHER INFORMATION: Synthetic Construct

<400> SEQUENCE: 3

Met Asn Asp Asn Val Ala Trp Phe Lys Gln Ala Lys Tyr Gly Met Met
1               5                   10                  15

Ile His Trp Gly Leu Tyr Ser Leu Leu Ala Gly Glu Tyr Arg Gly Glu
                20                  25                  30

Ser Ser Ser Ala Tyr Ala Glu Trp Ile Gln Ser Lys Phe Gln Ile Pro
                35                  40                  45

Asn Ala Glu Tyr Gly Asn Leu Ala Thr Ala Phe Asn Pro Leu Tyr Phe
            50                  55                  60

Asp Ala Lys Lys Ile Val Ala Leu Ala Lys Gln Cys Gly Met Gln Tyr
65                  70                  75                  80

Leu Val Val Thr Thr Lys His His Asp Gly Phe Ala Met Tyr His Ser
                85                  90                  95

Lys Val Asp Ala Tyr Asn Val Tyr Asp Ala Thr Pro Phe His Arg Asp
                100                 105                 110

Ile Ile Gly Glu Leu Ala Glu Ala Cys Gln Lys Ala Gly Leu Lys Phe
                115                 120                 125

Gly Leu Tyr Tyr Ser Gln Asp Leu Asp Trp His Asp Pro Asn Gly Gly
            130                 135                 140

Gly Tyr Lys Ser Asn Asp Val Glu Thr Ala Gly Thr Thr Trp Asp Asn
145                 150                 155                 160

Ser Trp Asp Phe Pro Asp Glu Asp Gln Lys Asn Phe Asp Leu Cys Phe
                165                 170                 175

Asp Asn Lys Ile Leu Pro Gln Ile Lys Glu Ile Met Ser Asn Tyr Gly
                180                 185                 190

Asp Ile Ala Thr Ala Trp Phe Asp Val Pro Met Thr Leu Ser Glu Ala
                195                 200                 205

Gln Ser Gln Thr Ile Tyr Asp Thr Val Arg Glu Leu Gln Pro Asn Cys
            210                 215                 220

Leu Ile Asn Ser Arg Leu Gly Asn Gly Lys Tyr Asp Phe Val Ser Leu
225                 230                 235                 240

Gly Asp Asn Glu Ile Pro Lys Asn Lys Glu Asp Met Asn Lys Thr Asp
                245                 250                 255

Val Asp Tyr Asn Glu Ile Thr Gly Phe Lys Pro Ser Pro Leu Gly Leu
                260                 265                 270

Tyr Gly Thr Ala Gly Thr Ile Asn Asp Ser Trp Gly Phe Ser Tyr His
            275                 280                 285

Asp Gln Asn Trp Lys Thr Pro Arg Thr Leu Tyr Arg Tyr Lys Gln His
                290                 295                 300

Leu Asn Asp Phe Gly Ile Asn Tyr Leu Leu Asn Val Gly Leu Asp Pro
```

Leu Gly Arg Val Pro Met Met Ala Glu Glu Asn Leu Leu Ala Ala Lys
              325                 330                 335

Ala Leu Glu Asp Glu Ala Asn Arg Leu
              340                 345

<210> SEQ ID NO 4
<211> LENGTH: 345
<212> TYPE: PRT
<213> ORGANISM: Lactobacillus casei

<400> SEQUENCE: 4

Met Asn Asp Asn Val Ala Trp Phe Lys Gln Ala Lys Tyr Gly Met Met
1               5                   10                  15

Ile His Trp Gly Leu Tyr Ser Leu Leu Ala Gly Glu Tyr Arg Gly Glu
                20                  25                  30

Ser Ser Ser Ala Tyr Ala Glu Trp Ile Gln Ser Lys Phe Gln Ile Pro
            35                  40                  45

Asn Ala Glu Tyr Gly Asn Leu Ala Thr Ala Phe Asn Pro Leu Tyr Phe
    50                  55                  60

Asp Ala Lys Lys Ile Val Ala Leu Ala Lys Gln Cys Gly Met Gln Tyr
65                  70                  75                  80

Leu Val Val Thr Thr Lys His His Asp Gly Phe Ala Met Tyr His Ser
                85                  90                  95

Lys Val Asp Ala Tyr Asn Val Tyr Asp Ala Thr Pro Phe His Arg Asp
            100                 105                 110

Ile Ile Gly Glu Leu Ala Glu Ala Cys Gln Lys Ala Gly Leu Lys Phe
        115                 120                 125

Gly Leu Tyr Tyr Ser Gln Asp Leu Asp Trp His Asp Pro Asn Gly Gly
    130                 135                 140

Gly Tyr Lys Ser Asn Asp Val Glu Thr Ala Gly Thr Thr Trp Asp Asn
145                 150                 155                 160

Ser Trp Asp Phe Pro Asp Glu Asp Gln Lys Asn Phe Asp Leu Cys Phe
                165                 170                 175

Asp Asn Lys Ile Leu Pro Gln Ile Lys Glu Ile Met Ser Asn Tyr Gly
            180                 185                 190

Asp Ile Ala Thr Ala Trp Phe Asp Val Pro Met Thr Leu Ser Glu Ala
        195                 200                 205

Gln Ser Gln Thr Ile Tyr Asp Thr Val Arg Glu Leu Gln Pro Asn Cys
    210                 215                 220

Leu Ile Asn Ser Arg Leu Gly Asn Gly Lys Tyr Asp Phe Val Ser Leu
225                 230                 235                 240

Gly Asp Asn Glu Ile Pro Lys Asn Lys Glu Asp Met Asn Lys Thr Asp
                245                 250                 255

Val Asp Tyr Asn Glu Ile Thr Gly Phe Lys Pro Ser Pro Leu Gly Leu
            260                 265                 270

Tyr Glu Thr Ala Gly Thr Ile Asn Asp Ser Trp Gly Phe Ser Tyr His
        275                 280                 285

Asp Gln Asn Trp Lys Thr Pro Arg Thr Leu Tyr Arg Tyr Lys Gln His
    290                 295                 300

Leu Asn Asp Phe Gly Ile Asn Tyr Leu Leu Asn Val Gly Leu Asp Pro
305                 310                 315                 320

Leu Gly Arg Val Pro Met Met Ala Glu Glu Asn Leu Leu Ala Ala Lys
                325                 330                 335

```
Ala Leu Glu Asp Glu Ala Asn Arg Leu
        340                 345

<210> SEQ ID NO 5
<211> LENGTH: 28
<212> TYPE: PRT
<213> ORGANISM: Artificial Sequence
<220> FEATURE:
<223> OTHER INFORMATION: Synthetic Construct

<400> SEQUENCE: 5

Val Trp Leu Asp Gly Ala Asn Gly Asn Glu Ala Gly Val Arg Asp Asn
1               5                   10                  15

Glu Thr Thr Val Ser Ser Gln Asp Ala Glu Val Asp
            20                  25

<210> SEQ ID NO 6
<211> LENGTH: 26
<212> TYPE: PRT
<213> ORGANISM: Artificial Sequence
<220> FEATURE:
<223> OTHER INFORMATION: Synthetic Construct

<400> SEQUENCE: 6

Phe Trp Phe Asp Gly Thr Trp Ala Asp Asp Lys Gly Met Gly Asp Tyr
1               5                   10                  15

Glu Glu Arg Arg Leu Pro Trp Glu Ala Cys
            20                  25

<210> SEQ ID NO 7
<211> LENGTH: 24
<212> TYPE: PRT
<213> ORGANISM: Artificial Sequence
<220> FEATURE:
<223> OTHER INFORMATION: Synthetic Construct

<400> SEQUENCE: 7

Ala Trp Phe Asp Val Pro Met Gly Leu Gly Asp Asn Glu Glu Ile Thr
1               5                   10                  15

Gly Phe Lys Pro Tyr Glu Thr Ala
            20

<210> SEQ ID NO 8
<211> LENGTH: 24
<212> TYPE: PRT
<213> ORGANISM: Artificial Sequence
<220> FEATURE:
<223> OTHER INFORMATION: Synthetic Construct

<400> SEQUENCE: 8

Ile Trp Ser Asp Gly Glu Trp Gly Cys Ser Cys His His Cys Glu Asp
1               5                   10                  15

Lys Phe Lys Pro Trp Glu Met Cys
            20

<210> SEQ ID NO 9
<211> LENGTH: 18
<212> TYPE: PRT
<213> ORGANISM: Artificial Sequence
<220> FEATURE:
<223> OTHER INFORMATION: Synthetic Construct

<400> SEQUENCE: 9

Leu Trp Asn Asp Met Gly Trp Gly Ala Glu Tyr His Val Pro Trp Glu
1               5                   10                  15
```

Phe Thr

<210> SEQ ID NO 10
<211> LENGTH: 6
<212> TYPE: PRT
<213> ORGANISM: Artificial Sequence
<220> FEATURE:
<223> OTHER INFORMATION: Synthetic Construct

<400> SEQUENCE: 10

Lys Leu Ala Asn Lys Thr
1               5

<210> SEQ ID NO 11
<211> LENGTH: 19
<212> TYPE: PRT
<213> ORGANISM: Artificial Sequence
<220> FEATURE:
<223> OTHER INFORMATION: Synthetic Construct

<400> SEQUENCE: 11

Gly Gln Asn Asp Thr Ser Gln Thr Ser Ser Pro Ser Leu Pro Lys Thr
1               5                   10                  15

Gly Gly Ser

<210> SEQ ID NO 12
<211> LENGTH: 34
<212> TYPE: PRT
<213> ORGANISM: Artificial Sequence
<220> FEATURE:
<223> OTHER INFORMATION: Synthetic Construct

<400> SEQUENCE: 12

Trp Met Glu Trp Asp Arg Glu Ile Asn Asn Tyr Thr Ser Leu Ile His
1               5                   10                  15

Ser Leu Ile Glu Glu Ser Gln Asn Gln Gln Glu Lys Asn Glu Gln Glu
            20                  25                  30

Leu Leu

<210> SEQ ID NO 13
<211> LENGTH: 33
<212> TYPE: PRT
<213> ORGANISM: Artificial Sequence
<220> FEATURE:
<223> OTHER INFORMATION: Synthetic Construct

<400> SEQUENCE: 13

Glu Ile Asn Cys Thr Arg Pro Asn Asn Asn Thr Arg Pro Gly Glu Ile
1               5                   10                  15

Ile Gly Asp Ile Arg Gln Ala His Cys Asn Ile Ser Arg Ala Lys Trp
            20                  25                  30

Asn

<210> SEQ ID NO 14
<211> LENGTH: 35
<212> TYPE: DNA
<213> ORGANISM: Artificial Sequence
<220> FEATURE:
<223> OTHER INFORMATION: Synthetic Construct

<400> SEQUENCE: 14
cgcgaccgcc tggttcgccg tgccgatgac gctgt                                35

<210> SEQ ID NO 15
<211> LENGTH: 35
<212> TYPE: DNA
<213> ORGANISM: Artificial Sequence
<220> FEATURE:
<223> OTHER INFORMATION: Synthetic Construct

<400> SEQUENCE: 15
acagcgtcat cggcacggcg aaccaggcgg tcgcg                              35

<210> SEQ ID NO 16
<211> LENGTH: 35
<212> TYPE: DNA
<213> ORGANISM: Artificial Sequence
<220> FEATURE:
<223> OTHER INFORMATION: Synthetic Construct

<400> SEQUENCE: 16
cgcgaccgcc tggttctccg tgccgatgac gctgt                              35

<210> SEQ ID NO 17
<211> LENGTH: 35
<212> TYPE: DNA
<213> ORGANISM: Artificial Sequence
<220> FEATURE:
<223> OTHER INFORMATION: Synthetic Construct

<400> SEQUENCE: 17
acagcgtcat cggcacggag aaccaggcgg tcgcg                              35

<210> SEQ ID NO 18
<211> LENGTH: 35
<212> TYPE: DNA
<213> ORGANISM: Artificial Sequence
<220> FEATURE:
<223> OTHER INFORMATION: Synthetic Construct

<400> SEQUENCE: 18
cgcgaccgcc tggttcggcg tgccgatgac gctgt                              35

<210> SEQ ID NO 19
<211> LENGTH: 35
<212> TYPE: DNA
<213> ORGANISM: Artificial Sequence
<220> FEATURE:
<223> OTHER INFORMATION: Synthetic Construct

<400> SEQUENCE: 19
acagcgtcat cggcacgccg aaccaggcgg tcgcg                              35

<210> SEQ ID NO 20
<211> LENGTH: 35
<212> TYPE: DNA
<213> ORGANISM: Artificial Sequence
<220> FEATURE:
<223> OTHER INFORMATION: Synthetic Construct

<400> SEQUENCE: 20
cgcgaccgcc tggttcaccg tgccgatgac gctgt                              35

<210> SEQ ID NO 21
<211> LENGTH: 35
<212> TYPE: DNA
<213> ORGANISM: Artificial Sequence
<220> FEATURE:
<223> OTHER INFORMATION: Synthetic Construct

<400> SEQUENCE: 21
acagcgtcat cggcacggtg aaccaggcgg tcgcg                                35

<210> SEQ ID NO 22
<211> LENGTH: 37
<212> TYPE: DNA
<213> ORGANISM: Artificial Sequence
<220> FEATURE:
<223> OTHER INFORMATION: Synthetic Construct

<400> SEQUENCE: 22
caccgctggg tctgtacgca accgcgggca cgattaa                              37

<210> SEQ ID NO 23
<211> LENGTH: 37
<212> TYPE: DNA
<213> ORGANISM: Artificial Sequence
<220> FEATURE:
<223> OTHER INFORMATION: Synthetic Construct

<400> SEQUENCE: 23
ttaatcgtgc ccgcggttgc gtacagaccc agcggtg                              37

<210> SEQ ID NO 24
<211> LENGTH: 37
<212> TYPE: DNA
<213> ORGANISM: Artificial Sequence
<220> FEATURE:
<223> OTHER INFORMATION: Synthetic Construct

<400> SEQUENCE: 24
caccgctggg tctgtactca accgcgggca cgattaa                              37

<210> SEQ ID NO 25
<211> LENGTH: 37
<212> TYPE: DNA
<213> ORGANISM: Artificial Sequence
<220> FEATURE:
<223> OTHER INFORMATION: Synthetic Construct

<400> SEQUENCE: 25
ttaatcgtgc ccgcggttga gtacagaccc agcggtg                              37

<210> SEQ ID NO 26
<211> LENGTH: 37
<212> TYPE: DNA
<213> ORGANISM: Artificial Sequence
<220> FEATURE:
<223> OTHER INFORMATION: Synthetic Construct

<400> SEQUENCE: 26
caccgctggg tctgtacgga accgcgggca cgattaa                              37

<210> SEQ ID NO 27
<211> LENGTH: 37
<212> TYPE: DNA
<213> ORGANISM: Artificial Sequence
<220> FEATURE:
<223> OTHER INFORMATION: Synthetic Construct

<400> SEQUENCE: 27
ttaatcgtgc ccgcggttcc gtacagaccc agcggtg                              37

<210> SEQ ID NO 28

<211> LENGTH: 30
<212> TYPE: DNA
<213> ORGANISM: Artificial Sequence
<220> FEATURE:
<223> OTHER INFORMATION: Synthetic Construct

<400> SEQUENCE: 28
ccgctgggtc tgtacgatac cgcgggcacg                              30

<210> SEQ ID NO 29
<211> LENGTH: 30
<212> TYPE: DNA
<213> ORGANISM: Artificial Sequence
<220> FEATURE:
<223> OTHER INFORMATION: Synthetic Construct

<400> SEQUENCE: 29
cgtgcccgcg gtatcgtaca gacccagcgg                              30

<210> SEQ ID NO 30
<211> LENGTH: 221
<212> TYPE: PRT
<213> ORGANISM: Artificial Sequence
<220> FEATURE:
<223> OTHER INFORMATION: Synthetic Construct

<400> SEQUENCE: 30

Leu Gly Ser Gly Lys Ile Leu His Asn Gln Asn Val Asn Ser Trp Gly
1               5                   10                  15

Pro Ile Thr Val Thr Pro Thr Thr Asp Gly Gly Glu Thr Arg Phe Asp
            20                  25                  30

Gly Gln Ile Ile Val Gln Met Glu Asn Asp Pro Val Val Ala Lys Ala
        35                  40                  45

Ala Ala Asn Leu Ala Gly Lys His Ala Glu Ser Ser Val Val Val Gln
    50                  55                  60

Leu Asp Ser Asp Gly Asn Tyr Arg Val Val Tyr Gly Asp Pro Ser Lys
65                  70                  75                  80

Leu Asp Gly Lys Leu Arg Trp Gln Leu Val Gly His Gly Arg Asp His
                85                  90                  95

Ser Glu Thr Asn Asn Thr Arg Leu Ser Gly Tyr Ser Ala Asp Glu Leu
            100                 105                 110

Ala Val Lys Leu Ala Lys Phe Gln Gln Ser Phe Asn Gln Ala Glu Asn
        115                 120                 125

Ile Asn Asn Lys Pro Asp His Ile Ser Ile Val Gly Cys Ser Leu Val
    130                 135                 140

Ser Asp Asp Lys Gln Lys Gly Phe Gly His Gln Phe Ile Asn Ala Met
145                 150                 155                 160

Asp Ala Asn Gly Leu Arg Val Asp Val Ser Val Arg Ser Ser Glu Leu
                165                 170                 175

Ala Val Asp Glu Ala Gly Arg Lys His Thr Lys Asp Ala Asn Gly Asp
            180                 185                 190

Trp Val Gln Lys Ala Glu Asn Asn Lys Val Ser Leu Ser Trp Asp Ala
        195                 200                 205

Gln Leu Glu Gly Gly Ser Gly Gly Ser Gly Asn Ser Gly
    210                 215                 220

<210> SEQ ID NO 31
<211> LENGTH: 231
<212> TYPE: PRT
<213> ORGANISM: Artificial Sequence
<220> FEATURE:
<223> OTHER INFORMATION: Synthetic Construct

<400> SEQUENCE: 31

```
Leu Gly Ser Gly Lys Ile Leu His Asn Gln Asn Val Asn Ser Trp Gly
1               5                   10                  15

Pro Ile Thr Val Thr Pro Thr Thr Asp Gly Gly Glu Thr Arg Phe Asp
            20                  25                  30

Gly Gln Ile Ile Val Gln Met Glu Asn Asp Pro Val Val Ala Lys Ala
        35                  40                  45

Ala Ala Asn Leu Ala Gly Lys His Ala Glu Ser Ser Val Val Val Gln
    50                  55                  60

Leu Asp Ser Asp Gly Asn Tyr Arg Val Val Tyr Gly Asp Pro Ser Lys
65                  70                  75                  80

Leu Asp Gly Lys Leu Arg Trp Gln Leu Val Gly His Gly Arg Asp His
                85                  90                  95

Ser Glu Thr Asn Asn Thr Arg Leu Ser Gly Tyr Ser Ala Asp Glu Leu
                100                 105                 110

Ala Val Lys Leu Ala Lys Phe Gln Gln Ser Phe Asn Gln Ala Glu Asn
            115                 120                 125

Ile Asn Asn Lys Pro Asp His Ile Ser Ile Val Gly Cys Ser Leu Val
        130                 135                 140

Ser Asp Lys Gln Lys Gly Phe Gly His Gln Phe Ile Asn Ala Met
145                 150                 155                 160

Asp Ala Asn Gly Leu Arg Val Asp Val Ser Val Arg Ser Ser Glu Leu
                165                 170                 175

Ala Val Asp Glu Ala Gly Arg Lys His Thr Lys Asp Ala Asn Gly Asp
            180                 185                 190

Trp Val Gln Lys Ala Glu Asn Asn Lys Val Ser Leu Ser Trp Asp Ala
            195                 200                 205

Gln Leu Glu Gly Gly Ser Gly Gly Ser Gly Asn Ser Gly His His His
        210                 215                 220

His His His His His His
225                 230
```

DESIGNER α 6-FUCOSIDASE MUTANTS ENABLE DIRECT CORE FUCOSYLATION OF INTACT N-GLYCOPEPTIDES AND N-GLYCOPROTEINS

CROSS-REFERENCE TO RELATED APPLICATIONS

This application is filed under the provisions of 35 U.S.C. § 371 and claims the priority of International Patent Application No. PCT/US17/046232 filed on Aug. 10, 2017 which in turn claims priority to U.S. Provisional Patent Application No. 62/373,151 filed on Aug. 10, 2016, the contents of which is hereby incorporated by reference herein for all purposes.

GOVERNMENT RIGHTS IN INVENTION

This invention was made with government support under Grant Number R01GM080374D awarded by the National Institutes of Health. The government has certain rights in the invention.

BACKGROUND OF THE INVENTION

Field of the Invention

The present invention provides for novel fucosidase mutants that server as fuco-ligases for core fucosylation of a range of biological glycopeptides and glycoproteins including intact therapeutic antibodies. The site specific mutants enable the transfer of fucose to a core GlcNAc-Asn residue useful for drug delivery and vaccine development.

Related Art

Asparagine-linked glycosylation, namely the N-glycosylation, is one of the most prevalent posttranslational modifications of proteins in mammals, which plays important roles in modulating the intrinsic properties and biological functions of the underlying proteins[1,2]. For example, the N-glycans attached can have a profound effect on protein's folding, stability, antigenicity, and immunogenicity[2,3]. On the other hand, the N-glycans can directly participate in a variety of biological recognition processes, including cell adhesion, host-pathogen interaction, cancer metastasis, and immune response[1,4-9]. While all mammalian N-glycans share a common oligosaccharide core structure, further decoration of the core, such as sialylation and fucosylation, adds another level of structural diversity in modulating biological functions.

N-acetylglucosamine (GlcNAc) moiety in the N-glycans, is an important modification of N-glycoproteins. Compelling data have shown that core-fucosylation of glycoproteins regulates a wide range of cellular functions. For example, many studies have revealed that increased core fucosylation is often associated with cancer progression[10-12] AFP-L3, the core-fucosylated α-fetoprotein has been approved by regulatory agency as a biomarker for hepatocellular carcinoma, a major form of liver cancer[13]. The roles of core-fucosylation in development has been demonstrated by the experiments that knockout of FUT8 gene in mouse models induces severe growth retardation and death during postnatal development[14]. Core fucosylation also directly modulates the biological activities of glycoproteins, such as the antibody dependent cellular cytotoxicity (ADCC) of therapeutic monoclonal antibodies[15], the signaling functions of growth factor receptors and adhesion molecules[14,16-20] and the antigen recognition of IgG B cell receptors[21]. On the other hand, structural studies have suggested that core-fucosylation could significantly affect the conformations of N-glycans[22,23].

Given the difficulties to isolate homogeneous glycoforms from natural sources, synthesis of structurally well-defined, core-fucosylated glycopeptides and glycoproteins is essential for various glycomic studies aiming to further decipher the structural and functional impact of core-fucosylation[24-26]. In animals and humans, core-fucosylation is catalyzed solely by the mammalian α-1,6-fucosyltransferase, FUT8[27,28]. However, FUT8 has a very strict substrate specificity, requires the presence of a free GlcNAc at the α1,3-linked mannose arm in the N-glycan as the substrate, and usually is unable to fucosylate full-size mature N-glycans[29-32], although our recent study indicated that FUT8 could catalyze in vitro fucosylation of some high-mannose N-glycans lacking a free GlcNAc at the α1,3-linked mannose arm when present in an appropriate protein context[33]. This strict substrate specificity makes the α1,6-fucosyltransferase of limited usefulness for chemoenzymatic synthesis. On the other hand, chemical synthesis of core-fucosylated N-glycopeptides and N-glycoproteins is more complex than the synthesis of those non-fucosylated glycoconjugates, due to the difficulty in control of the α-stereo-selectivity in glycosylation and the acid-labile nature of the α1,6-fucosidic linkage[34,35]. Thus, a method for direct fucosylation of intact glycopeptides and glycoproteins is highly desirable.

SUMMARY OF THE INVENTION

Core fucosylation of N-glycoproteins plays a crucial role in modulating the biological functions of glycoproteins. Yet, the synthesis of structurally well-defined, core-fucosylated glycoproteins remains a challenging task due to the complexity in multi-step chemical synthesis or the inability of the biosynthetic α1,6-fucosyltransferase (FUT8) to directly fucosylate full-size mature N-glycans in a chemoenzymatic approach. The present invention provides for the design and generation of potential α1,6-fucosynthase and fucoligase for direct core-fucosylation of intact N-glycoproteins. Mutants with a mutation at the general acid/base residue E274 of the Lactobacillus casei α1,6-fucosidase, were able to efficiently fucosylate a wide variety of complex N-glycopeptides and intact glycoproteins. Testing results on the substrate specificity revealed that the α1,6-fucosidase mutants could introduce an α1,6-fucose moiety specifically at the Asn-linked GlcNAc moiety not only to GlcNAc-peptide, but also to high-mannose and complex type N-glycans in the context of N-glycopeptides, N-glycoproteins, and intact antibodies. This discovery opens a new avenue to a wide variety of homogeneous, core-fucosylated N-glycopeptides and N-glycoproteins that are hitherto difficult to obtain for structural and functional studies.

The present invention provides the discovery of novel mutants derived from Lactobacillus casei α-fucosidase, which are able to use α-fucosyl fluoride as the substrate for direct core-fucosylation of intact N-glycopeptides and N-glycoproteins without product hydrolysis. It has been found that the rationally designed mutants, E274A (SEQ ID NO: 1), E274S (SEQ ID NO: 2) and E274G (SEQ ID NO:3) derived from Lactobacillus casei α-fucosidase (SEQ ID NO: 4) carrying a single mutation at the general acid/base residue (E274) acted as a fucoligase and were able to fucosylate a wide variety of substrates including large synthetic N-glycopeptides, natural N-glycoproteins, and intact monoclonal antibodies.

In one aspect, the present invention provides for fucosylation activity of α1-6-fucosidase mutants of *Lactobacillus casei* (SEQ ID NO: 4), wherein the mutants have at least 95% homology thereto and exhibit fucosylation activity on nonfucosylated N-acetylglucosamine (GlcNAc) acceptor, wherein the fucosidase mutants enable the transfer of fucose to the nonfucosylated GlcNAc acceptor.

In another aspect, the present invention provides for α1-6-fucosidase mutants that show remarkably enhanced fucosylation efficiency and diminished or abrogated product hydrolytic activity relative to the wild type enzyme. Enzyme mutants preferably include site-specific mutations including a mutation at E274. The mutant enzymes include, but are not limited to, E274A, E274S, E274G, E274T, E274C, E274I, E274L, E274M, E274F, E274W, E274Y and E274V or fragments thereof derived from *Lactobacillus casei* fucosidase (AlfC) that include the catalytic domain and exhibit increased transfucosylation and reduced hydrolysis related to the wild type protein. Preferably the mutant proteins include E274A (SEQ ID NO: 1), E274S (SEQ ID NO: 2) and E274G (SEQ ID NO: 3).

Notably α1,6-fucosidase fragments and domains that carry a mutation at the E274 site are included in the present invention wherein any such domains and fragments may be fused to other proteins including, but not limited to, cysteine protease domain (CPD) (SEQ ID NO: 30), Fc, poly histidine (HIS), CPD and HIS (SEQ ID NO: 31) or gluathione S-transferase (GST), etc. The catalytic domain and the specific site of mutation are critical for the enzymatic activity, and thus, other sites on the enzyme may be modified or truncated, such as a terminus without negative effects of the transfucosylation activity.

In yet another aspect, the present invention provides for a method for fucosylating a N-glycopeptide or N-glycoprotein, the method comprising:
providing a GlcNAc containing peptide or protein as an GlcNAc acceptor;
providing an α-fucosyl fluoride (αFUCF) for access to a sugar fucose;
providing an α1,6-fucosidase mutant enzyme for enzymatically transfucosylating the αGlcNAc acceptor with the sugar fucose, wherein the α1,6-fucosidase mutant enzyme is a *Lactobacillus casei* α-fucosidase mutant.

In a still further aspect, the present invention provides two catalytic ways to attain core fucosylated glycopeptides and glycoproteins, including: 1) core fucosylation of GlcNAc-peptides or proteins and then transglycosylation of oligosaccharides to form fucosylated glycopeptides and glycoproteins; 2) transglycosylation of oligosaccharides to GlcNAc-peptides or proteins and then core fucosylation to form the fucosylated glycopeptides and glycoproteins.

In another aspect, the present invention provides for a chemoenzymatic method for the preparation of homogeneous fucosylated glycopeptides or glycoproteins, comprising:
providing an nonfucosylated GlcNAc acceptor; and
reacting the acceptor with a donor substrate including an activated fucose containing moiety, in the presence of a *Lactobacillus casei* α1-6-fucosidase E274 mutant protein or fragment thereof that includes the catalytic domain and exhibits increased transfucosylation and reduced hydrolytic activity relative to the wild type α1-6-fucosidase E274 enzyme to transfer the activated fucose containing moiety to the acceptor and yield the homogeneous fucosylated glycopeptides or glycoproteins.

Further the chemoenzymatic method of the present invention in the synthesis of homogeneous glycopeptides and glycoproteins may include combining α1,6-fucosidase mutants catalyzed core fucosylation and endo-N-acetylglycosaminidases catalyzed transglycosylation. Still further, the homogeneous glycopeptides and glycoproteins may include glycans attached to the peptides or proteins including but not limited to high mannose type, sialylated and asialo-complex type, hybrid type and their analogs.

The nonfucosylated glycopeptides or glycoproteins may include one or more Asn(asparagine)-linked GlcNAc moieties or more N-glycan sites, thus allowing introduction of one or multiple core fucoses by the chemoenzymatic method of the present invention.

Glycoproteins that may be fucosylated by the present invention, include but not limited to, a group of monoclonal antibodies consisting of 17b, 48d, A32, C11, 2G12, F240, IgG1b12, 19e, X5, TNX-355, cetuximab, rituximab, muromonab-CD3, abciximab, daclizumab, basiliximab, palivizumab, infliximab, trastuzumab, gemtuzumab ozogamicin, alemtuzumab, ibritumomab tiuxetan, adalimumab, omalizumab, tositumomab, 1131 tositumomab, efalizumab, bevacizumab, panitumumab, pertuzumab, natalizumab, etanercept, IGN101, voloximab, Anti-CD80 mAb, Anti-CD23 mAb, CAT-3888, CDP-791, eraptuzumab, MDX-010, MDX-060, MDX-070, matuzumab, CP-675,206, CAL, SGN-30, zanolimumab, adecatumumab, oregovomab, nimotuzumab, ABT-874, denosumab, AM 108, AMG 714, fontolizumab, daclizumab, golimumab, CNTO 1275, ocrelizumab, HuMax-CD20, belimumab, epratuzumab, MLN1202, visilizumab, tocilizumab, ocrerlizumab, certolizumab pegol, eculizumab, pexelizumab, abciximab, ranibizimumab, mepolizumab and MYO-029.

Further the acceptor peptide may include, but not limited to, N-acetylglucosaminyl N-fluorenylmethyloxycarbonyl asparagine (GlcNAc-FmocAsn), alpha-fetoprotein (AFP), heptoglobin, a synthetic glycol-V3 loop derived from HIV envelope glycoprotein gp120, an intact or glycoengineered recombinant IgG, an intact or glycoengineered ribonuclease (RNase B), erythropoietin (EPO), CD52 dodecapeptide, CD52SS, a sialylglycopeptide (SGP) hexapeptide or asialo-glycopeptide.

Another aspects of the present invention provides for activated glycosyl donor moieties including but not limited to an appropriate glycosyl fluoride, glycosyl azide and aryl glycoside sugar, e. g., αFucF, α fucosyl chloride, α fucosyl azide, 4 nitrophenyl α fucoside, 3 nitrophenyl α fucoside, 3,4 dinitrophenyl α fucoside, 4 methylumbelliferyl α fucoside.

It is further envisioned that the recombinant α1,6 fucosidase mutants are derived not only from *Lactobacillus casei*, but also include *Bacteroides fragilis, Elizabethkingia miricola, Aspergillus niger, Chryseobacterium meningosepticum* and *Homo sapiens* A1.

In a still further aspect, the enzymatic fucosylated glycopeptides and glycoproteins synthesized by the methods of the present invention using *Lactobacillus casei* α1,6 fucosidase E274 mutants may be used as biomarkers for cancer and/or other diseases and used in the testing of drugs to determine efficiency.

In yet another aspect, the present invention provides a substantially homogeneous preparation of core fucosylated glycopeptides or glycoproteins, wherein the substantially homogeneous preparation is produced by any of the aforementioned methods. Also provided are compositions comprising such homogeneous preparations.

In another aspect, the present invention provides for a method of treatment using a remodeled antibody having a desired fucosylation state and/or sialylated in an amount sufficient to modulate biological activity in a treated subject.

In a further aspect, the present invention provides for a kit including a least one *Lactobacillus casei* α-fucosidase mutant selected from the group consisting of E274A (SEQ ID NO: 1), E274S (SEQ ID NO: 2) and E274G (SEQ ID NO: 3).

In another aspect, the present invention provides for mutated α1-6-fucosidase enzyme selected from the group consisting of E274A (SEQ ID NO: 1), E274S (SEQ ID NO: 2) and E274G (SEQ ID NO: 3).

Other aspects, features and embodiments of the invention will be more fully apparent from the ensuing disclosure and appended claims.

BRIEF DESCRIPTION OF THE FIGURES

FIG. 21 A) ESI-MS of the Fuc α1,6-GlcNAc-RNase (23); FIG. 21 B) ESI-MS of the core-fucosylated complex type RNase C (25)

DETAILED DESCRIPTION OF THE INVENTION

Figure 1:
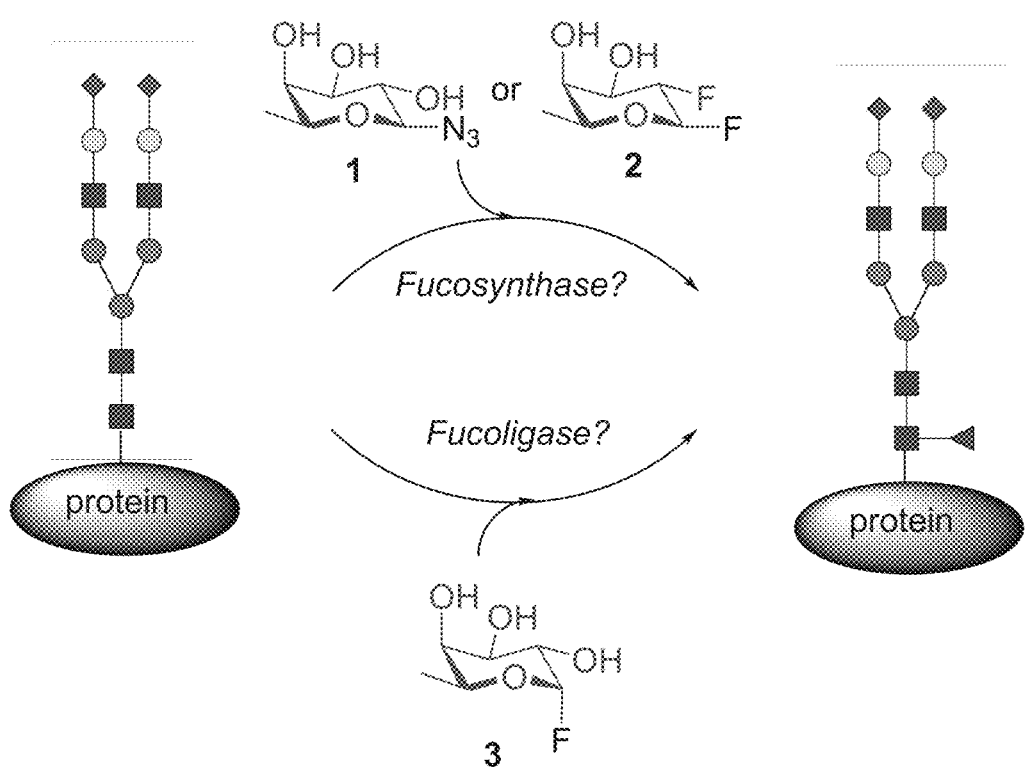
FIG. 1 shows the evaluation of fucosidase mutants for direct core fucosylation of N-glycans.

The present invention described herein is for novel fucosidase mutants that serve as fuco-ligases for core fucosylation of a range of biologically important glycopeptides and glycoproteins including intact therapeutic antibodies. Previously, there was no general method that can perform direct core-fucosylation of mature complex glycoproteins. The natural α 1,6-fucosyltransferases can only glycosylate limited intermediate N-glycan during biosynthesis and cannot add fucose to mature complex glycoproteins. The present invention solves a long-standing problem for direct enzymatic core-fucosylation of synthetic glycopeptides and recombinant glycoproteins. This invention also includes a series of fucosidase mutants including E274A, E274S and E274G, derived from *Lactobacillus casei* α-(1,6)-fucosidase (AlfC). These site-specific mutants enable the transfer of fucose from simple synthetic substrate α-fucosyl fluoride to the core GlcNAc-Asn residue in complex glycopeptides and glycoproteins including antibodies. Since core-fucosylation of glycoproteins is important for cancer progression and metastasis, and is critical for antibody effector functions, the present invention has wide applications for drug discovery and vaccine development.

The present invention provides for generating generate glycosidase mutants capable of using simple glycosyl donors for direct core-fucosylation of intact N-glycopeptides and N-glycoproteins, which could not be achieved by the catalysis of the biosynthetic α-1,6-fucosyltransferase (FUT8) because of its strict substrate specificity. To create such enabling mutants, two general glycosidase engineering strategies have been attempted. One is the glycosynthase concept through site-directed mutagenesis at the critical nucleophilic residue of a retaining glycosidase to generate a mutant that is devoid of hydrolysis activity but can take an activated glycosyl donor (usually a glycosyl fluoride) with an opposite anomeric configuration for transglycosylation[36-38]. Glycosynthases derived from several GH family glycosidases have been successfully created using this strategy[39-43]. The other is the glycoligase approach, first developed by Withers and co-workers, in which the general acid/base residue of a retaining glycosidase is mutated to eliminate the hydrolysis activity, and the enzymatic transglycosylation is enabled by using an activated glycosyl donor with the same anomeric configuration[44-47]. For β-glycosynthases derived from the corresponding retaining β-glycosidases, the readily synthesized and relatively stable α-glycosyl fluorides have become the common glycosyl donors[39,40] However, the evaluation of the transglycosylation activity of potential α-fucosynthases usually requires the β-fucosyl fluoride, which is quite unstable in aqueous solution and will be hydrolyzed spontaneously with a half-life of ca. 20 min[48]. Previously several α1,2- and α1,3-1,4-fucosynthases have been generated from the *Bifidobacterium bifidum* α-L-fucosidases and examined for enzymatic transfucosylation of glycoconjuagtes, but the dependence on the use of the highly unstable β-glycosyl fluoride renders these mutants less attractive for synthetic purpose[48-51]. As an alternative approach, Moracci and co-workers have shown that the stable β-fucosyl azide could serve as a glycosyl donor for the α-fucosynthases derived from the hyperthermophilic archaeon *Sulfolobus solfataricus* α-L-fucosidase[52]. This β-glycosyl azide was also successfully applied as a substrate for an α-galactosynthase[53,54].

Despite these successes, no α1,6-fucosynthase or any α-fucoligase has been reported so far. To explore this possibility, the present invention was started by choosing the α1,6-fucosidase from *Lactobacillus casei* (AlfC) as the model enzyme, which was shown to hydrolyze specifically α1,6-fucosidic linkage[55] and was recently reported to have transglycosylation activity, capable of making Fucα1,6GlcNAc disaccharide, using p-nitrophenyl α-fucoside as the donor substrate and GlcNAc as the acceptor[56,57]. Nevertheless, the wild type enzyme also hydrolyzes the disaccharide product rapidly leading to low synthetic efficiency. Moreover, it has been unclear if this enzyme could act on more complex substrates for transglycosylation other than a simple GlcNAc substrate. Thus, the present design is to generate potential glycosynthase and glycoligase mutants from the *Lactobacillus casei* α1,6-fucosidase, and to test their ability to core-fucosylate various acceptor substrates (FIG. 1). For evaluating the potential glycosynthase mutants, the stable β-fucosyl azide (1)[52] was used as the substrate. In addition, it was sought to synthesize the 2-deoxy-2-fluoro-β-fucosyl fluoride (2) as a more stable substrate to test the potential fucosynthase mutants. For evaluating the potential glycoligase mutants, the α-fucosyl fluoride (3) would be used as a substrate.

Alignment of Amino Acid Sequence with GH29 α-Fucosidases.

Figure 2:
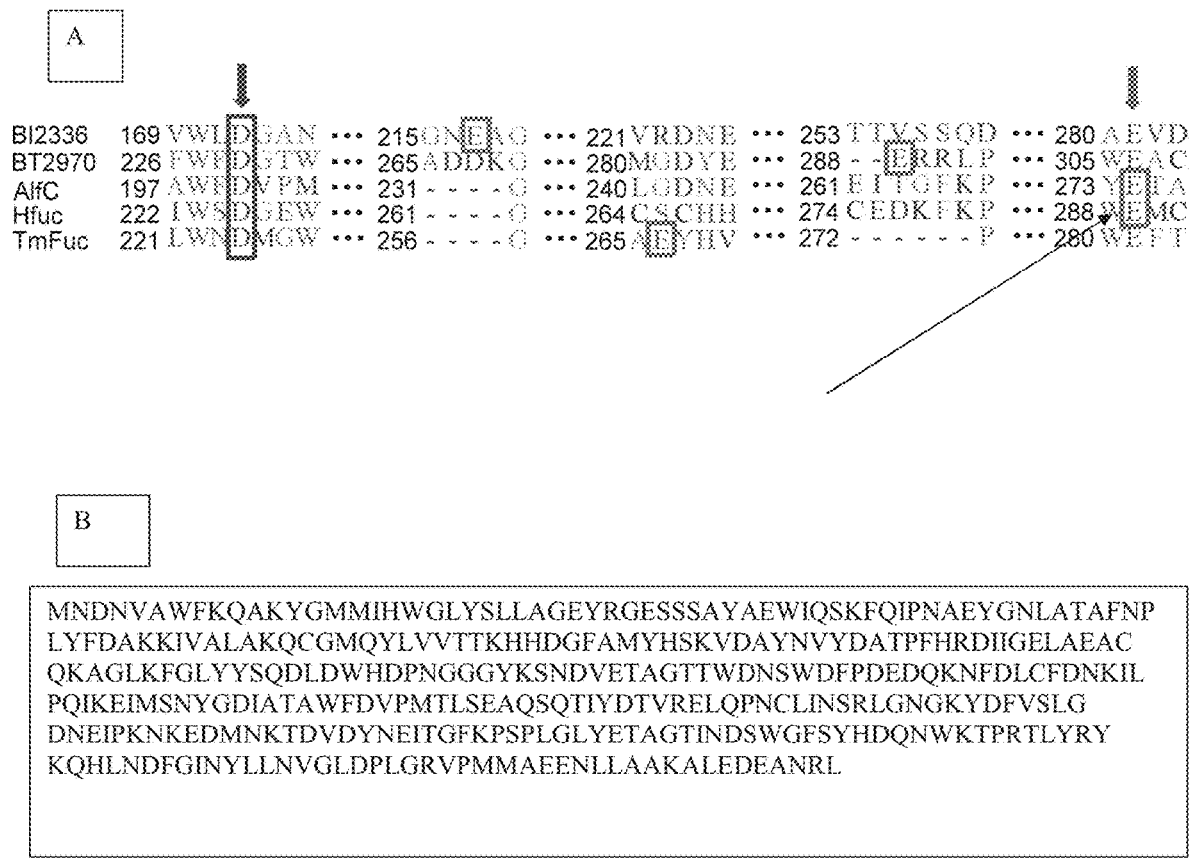
FIG. 2A shows the sequence alignment of AlfC and selected GH29 fucosidases including human α1,6-fucosidase (Hfuc). The left most arrow above the alignment and box beneath indicate the fully conserved nucleophile site across GH29 family. The right most arrow above the alignment shows the experimentally confirmed general acid/base site E289 for Hfuc. The box below the right most arrow indicates that the E274 of AlfC aligns with the E289 of Hfuc. B12336 (SEQ ID NO: 5), BT2970 (SEQ ID NO: 6), AlfC (SEQ ID NO: 7), Hfuc (SEQ ID NO: 8) and TMFFUC (SEQ ID NO: 9).
FIG. 2B shows SEQ ID NO: 4.

GH29 retaining α-L-fucosidases catalyze the removal of non-reducing terminal L-fucose residues in the α1,2, α1,3, α1,4, or α1,6-glycosidic linkages in oligosaccharides and glycoconjugates. In order to determine the key catalytic residues of AlfC α-fucosidase, several α-fucosidases belonging to the GH29 family were chosen in alignment of amino acid sequences, due to their distinct substrate specificities and positions of the two catalytic residues clarified in previous reports[58-61]. The results were shown in FIG. 2. All the positions of catalytic nucleophile, an aspartate residue, turned out to be completely aligned up among the five α-fucosidases including AlfC (Indicated by blue arrowhead and box in FIG. 2). It has been previously shown that the nucleophile residue is fully conserved across the GH29 family[62]. Thus residue D200 in AlfC which is aligned with the nucleophilic residues of the other GH29 family enzymes was very likely the nucleophile residue of the AlfC enzyme. The positions of general acid/base seemed more complicated, as these residues scattered around in these enzyme sequences (Indicated by purple box in FIG. 2). The glutamate residue E274 of AlfC aligned with the E289 of *Homo sapiens* A1 (Hfuc), while no polar amino acid residue of AlfC showed up at the positions of the general acid/base residues in other α-fucosidases. Interestingly, both Hfuc and AlfC turned out to be α1,6-fucosidases. Considering the alignment results and the substrate specificity, we assumed that the E274 residue could be the catalytic general acid/base residue for the AlfC enzyme.

Generation of Potential α-Fucosidase-Based Glycosynthases and Glycoligases.

Figure 11:
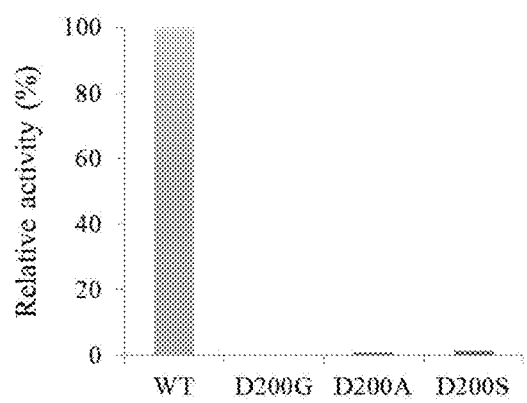
FIG. 11 shows the comparison of the hydrolytic activity of wild-type AlfC α-fucosidase and its mutants.
Figure 11:
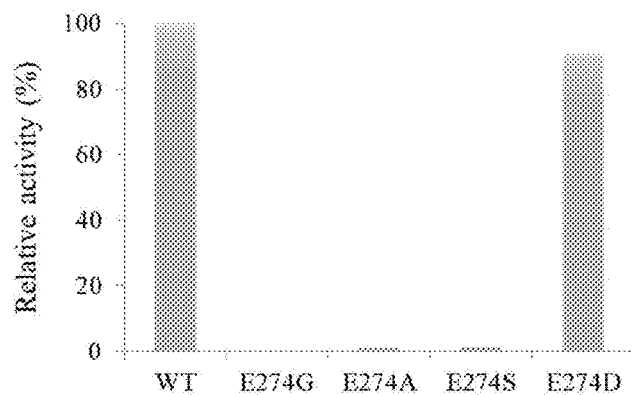

Following the glycosynthase concept proposed by Withers and co-workers[36], site-directed mutagenesis was performed at the identified nucleophile in the AlfC α1,6-fucosidase, D200, to generate selected mutants, including D200G, D200S, D200A, and D200S. Similarly, selected mutants at the putative general acid/base residue, E274, were generated to provide potential glycoligases, including E274A, E274S, E274G, and E274D (Table 1 provides the primer pairs for such mutant SEQ ID NO: 14 to 29). These mutants were expressed as a fusion protein with a C-terminal *Vibrio cholera* MARTX toxin cysteine protease domain (CPD) carrying a 10×His tag (SEQ ID NO: 31), as previous experiments have demonstrated that the CPD tag (SEQ ID NO: 30) can enhance the solubility and stability of recombinant proteins[63-66]. All these mutants were efficiently expressed in *E. coli* with a relatively high yield (more than 40 mg/L) and were readily purified by Nickel-NTA affinity chromatography[63]. The hydrolysis activity of these mutants was tested together with wild type AlfC using p-nitro α-fucoside (pNPFuc) as the substrate. As expected, all these mutants, except E274D, showed only trace residual hydrolysis activity due to the mutations at the critical residues, while (FIG. 11). This study confirms that the D200 residue is the nucleophile and that the E274 residue is most likely the general acid/base residue. In the case of E294D, the similarity between the Glu and Asp suggests that the Asp residue in place of the E274 could still play the role of the Glu residue as the general acid/base for promoting hydrolysis of the substrate.

Assessment of the Mutants as Potential Glycosynthases or Glycoligases.

Figure 3:
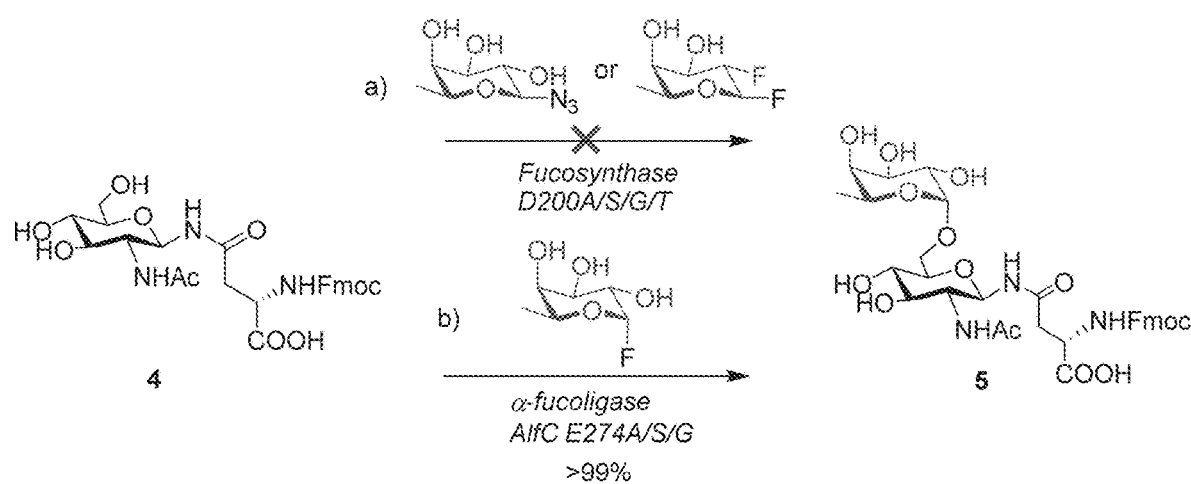
FIG. 3 shows the scheme for transglycosylation with potential α-fucosylation and α-fucoligase.
Figure 10:
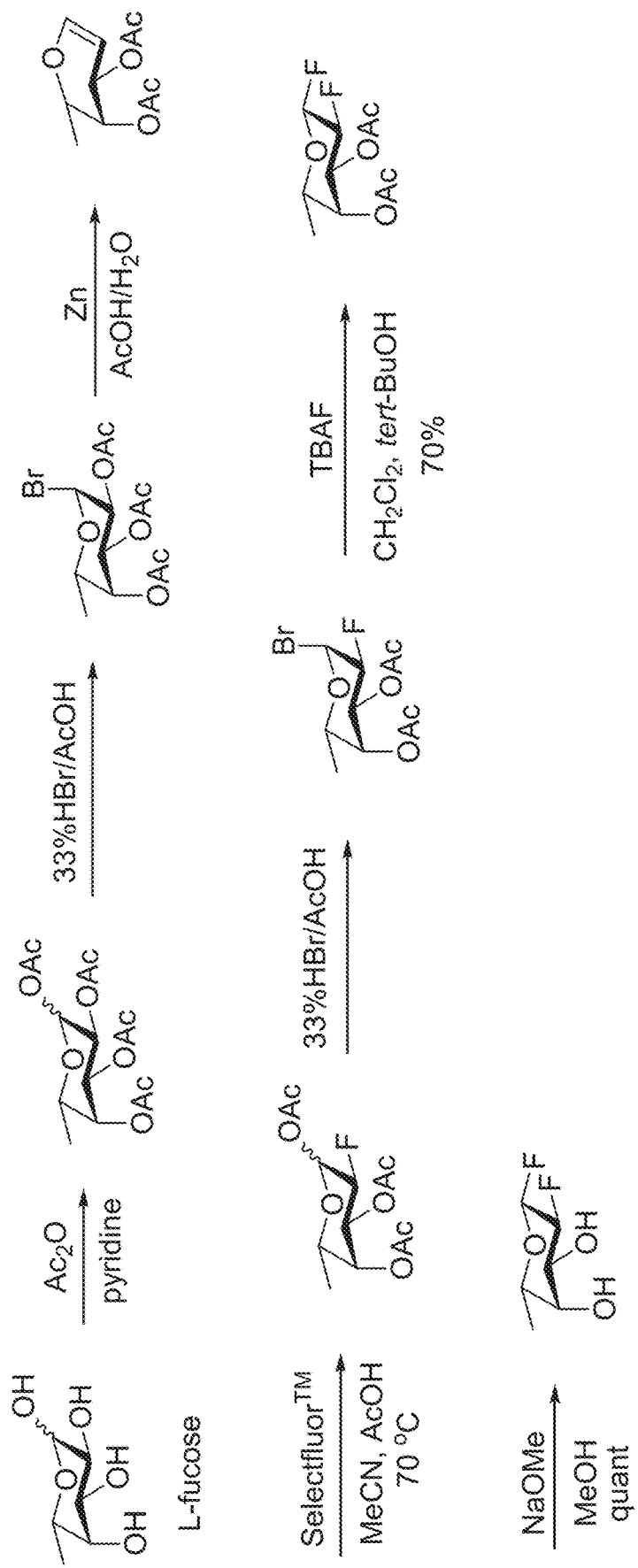
FIG. 10 shows Synthesis of 2-deoxy-2-fluoro-α-L-fucopyranosyl fluoride (2). Characterization of 2: $^1$H NMR (D$_2$O, 400 MHz): δ=5.10 (m, 1H, H-1), 4.41 (m, 1H, H-2), 3.66 (m, 3H, H-5, H-4, H-3), 1.32 (d, 3H, —CH$_3$). $^{13}$C NMR (D$_2$O, 100 MHz): δ=107.53 (C-1), 91.47 (C-2), 71.76 (C-4), 7157 (C-5), 71.32 (C-3), 15.78 (—CH$_3$). ESI-MS: calc. for 2, M=168.1 Da, found (m/z), 169.1 [M+H]$^+$, 191.1 [M+Na]$^+$; HR-MS: [M+Na]$^+$ calc. for C$_6$H$_{10}$O$_3$F$_2$Na, 191.0924, found (m/z), 191.0948.

Initially, the D200 mutants were examined as potential glycosynthases using two types of activated fucosyl donors with opposite anomeric configuration as substrates. For nucleophile mutant such as D200G, a fucosyl fluoride with reversed anomeric configuration, β-fucosyl fluoride or β-fucosyl azide, should be applied to mimic the enzyme-substrate intermediate[52,53,67]. However, β-glycosyl fluorides are quite unstable and are subjected to spontaneous hydrolysis in aq. solutions[42]. Indeed, most successful glycosynthases have been derived so far from retaining β-glycosidases that take the α-glycosyl fluoride as donor substrate. To overcome this problem, 2-deoxy-2-fluoro-β-fucosyl fluoride (2) was synthesized as a more stable substrate (FIG. 10)[68]. The stability was tested in a buffer and found that the half-life of 2 was 6 h at 37° C. in a phosphate buffer (100 mM, pH 7.4), which was significantly more stable than the corresponding β-fucosyl fluoride ($t_{1/2}$ ca. 20 min)[68]. β-Fucosyl azide (1) was used before as substrate for testing α-1,2- and α-1,3-fucosidase mutants[52]. Thus, the potential glycosylation activity of the nucleophilic mutants, including D200G, D200S, D200A, and D200S, were tested using both the β-glycosyl azide (1) and the β-glycosyl fluoride (2) as the donor substrates and the Fmoc-Asn(GlcNAc)-OH (4)[69] as the acceptor substrate (FIG. 3). The reactions were run with different amounts of enzymes and were monitored by reverse-phase HPLC analysis. However, no glycosylation products were observed with either the β-fucosyl azide (1) or the 2-dexoy-2-fluoro-β-fucosyl fluoride (2) donors by any of the nucleophilic mutants. This study suggested that those nucleophilic mutants so far tested did act as a glycosynthase.

Next, the potential glyco-ligase activity was tested of the general acid/base residue mutants using the α-fucosyl fluoride (3) as the donor substrate (FIG. 3). Interestingly, the E274A mutant exhibited excellent catalytic activity to transfer a fucose residue to the GlcNAc moiety of acceptor 4 to give the disaccharide derivative (5) with regio- and stereo-specificity (FIG. 3). Using a moderate excess of the fucosyl fluoride (donor/acceptor, 2:1 molar equivalent), an almost quantitative yield of product 5 was achieved by incubation of E274A (0.1 mg/ml, pH 7.5) with 3 and 4 at 42° C. within 1 h. The other two mutants, E274G and E274S, were also excellent catalysts for fucosylation and gave similar results.

Figure 12:
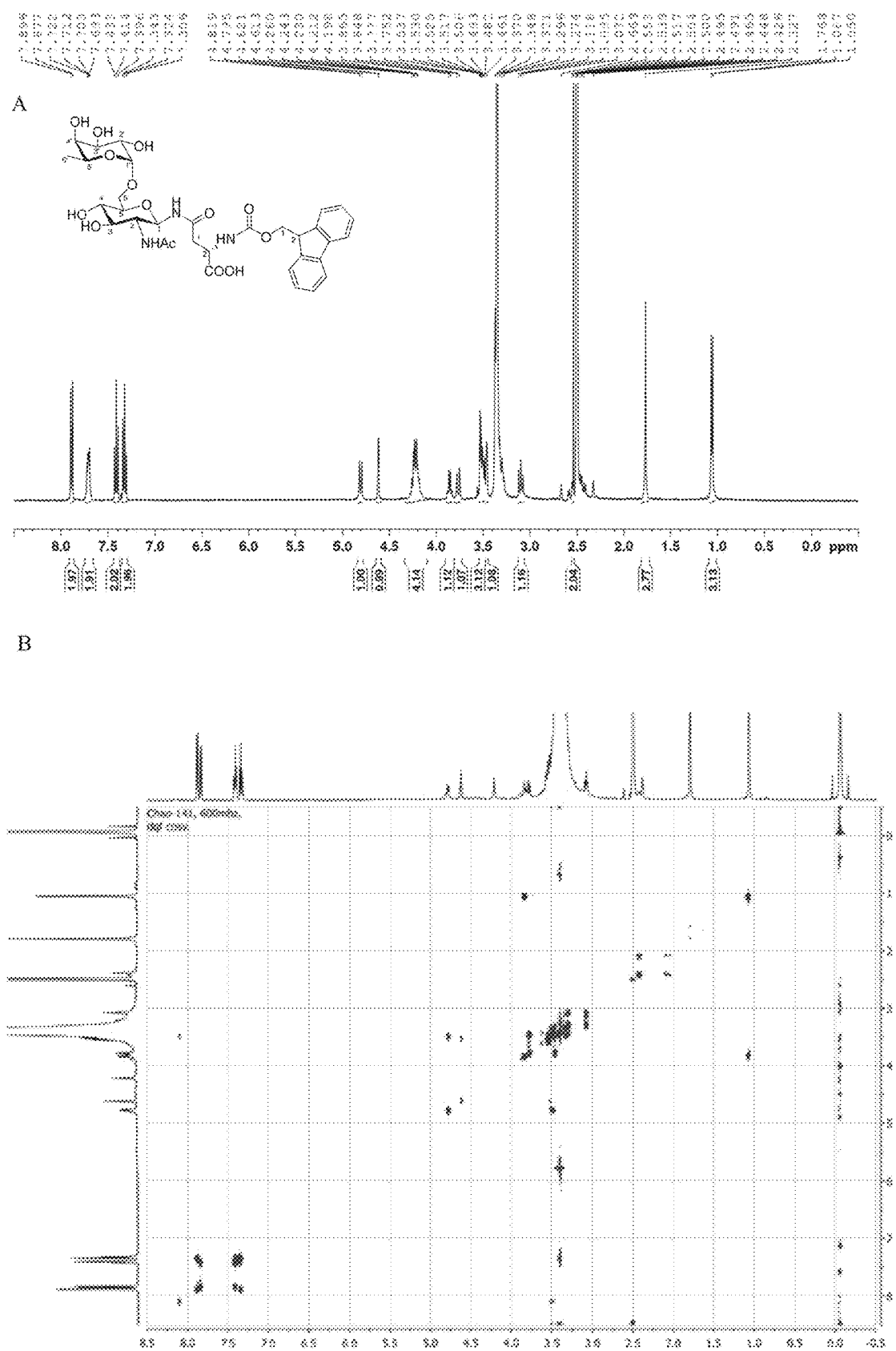
FIGS. 12 A and B shows the $^1$H NMR spectrum of the fucosylated product (5). A) $^1$H-NMR; B) $^1$H-$^1$H COS Y spectrum.

The structure of 5 was confirmed by ESI-MS (calculated, M=703.3 Da; found, 704.5 [M+H]$^+$) and $^1$H-$^1$H COS Y NMR (FIG. 12). A doublet at δ 4.62 with a relatively small coupling constant (J=3.2 Hz) for the H-1 of the fucose moiety suggested that the attached fucose was in an α-glycosidic linkage. On the other hand, an obvious shift for the H-6 in the GlcNAc moiety of 5 toward the low field (from δ3.6 in 4 to δ3.8 in 5), while other protons on the GlcNAc moieties in 4 and 5 did not show obvious change, suggested that the fucosylation occurred at the 6-hydroxy group of the GlcNAc moiety to form an α-1,6-fucosyl glycosidic linkage.

Figure 13:
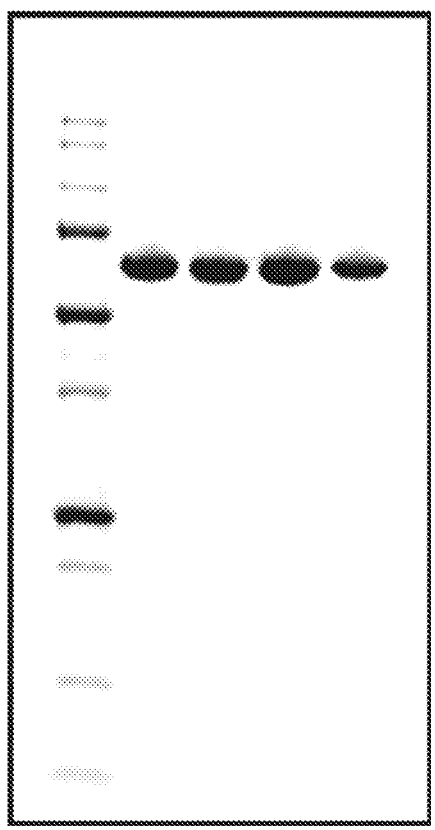
FIG. 13 shows the SDS-PAGE of AlfC α1,6-fucosidase mutants. A) lane M, protein ladder; lane A, mutant E274A; lane S, mutant E274S; lane G, mutant E274G and lane D, mutant E274D. B) lane+, AlfC mutant E274A with CPD tag; lane−, AlfC mutant E274A without CPD tag.
Figure 13:
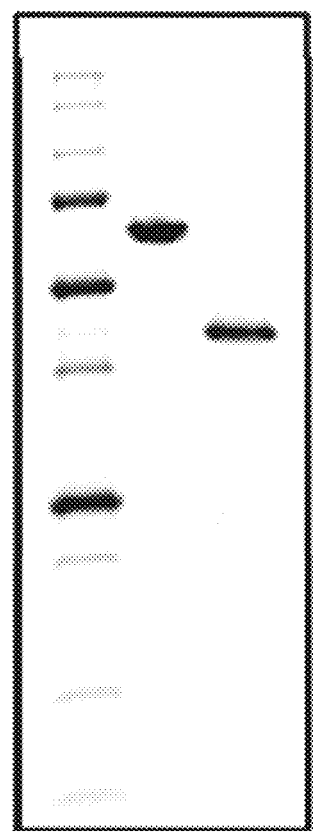
Figure 14:
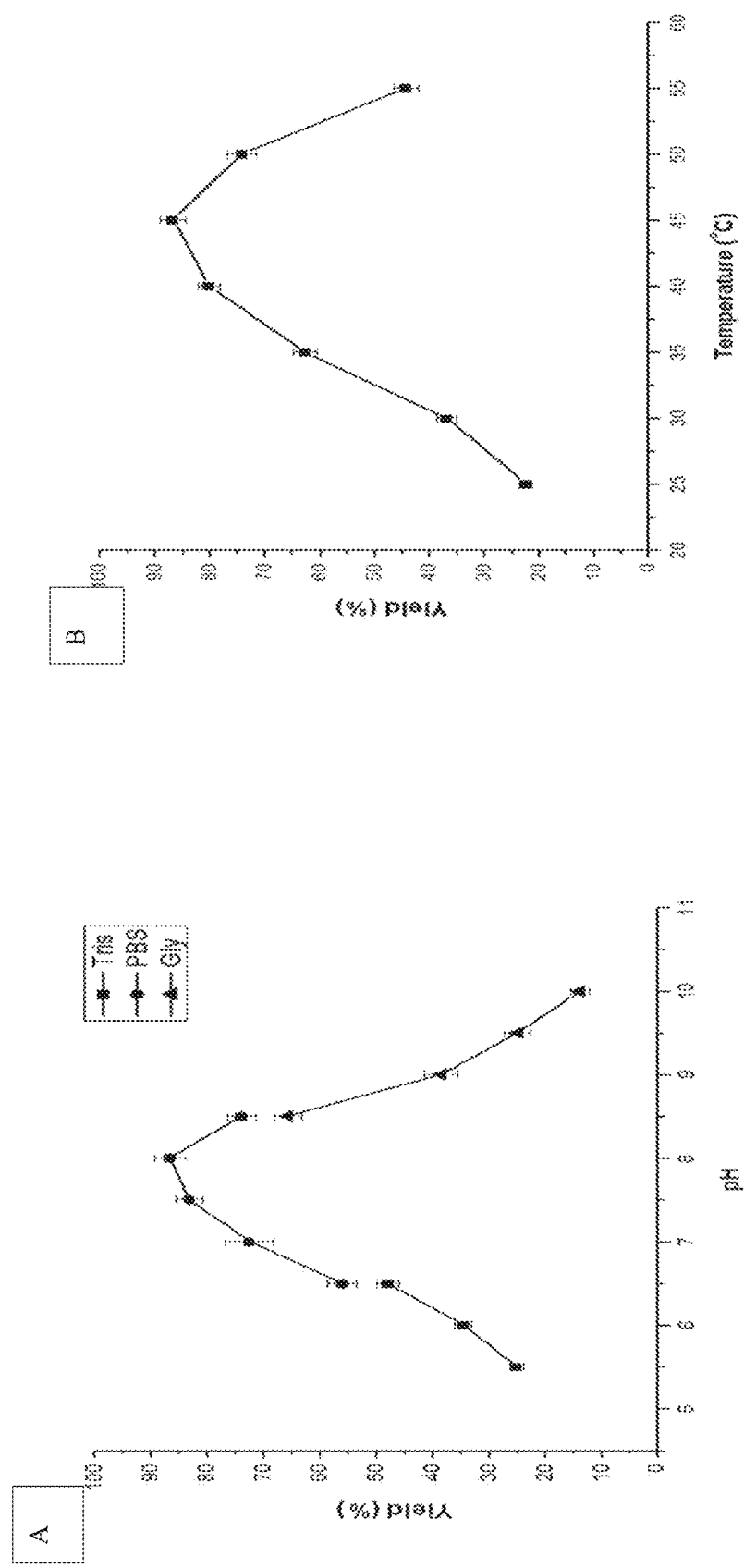
FIG. 14 shows the catalytic profiles of AlfC E274A under different conditions. A) pH profile; B) temperature profile of its catalysis. To investigate pH profile of AlfC α-fucosidase in transglycosylation reaction, a mixture of the donor sugar (3) (20 mM), acceptor sugar (4) (10 mM) and enzyme AlfC E274A (0.2 mg/mL) was incubated in the respective buffer at 42° C. for 20 min, including Tris-HCl (0.1 M, pH5.5-6.5), PBS (0.1 M, pH6.5-8.5) and glycine-NaOH (0.1 M, pH8.5-10.0), all contains 5% DMSO. The transglycosylation product was quantitated by HPLC analysis. To investigate temperature profile of AlfC α-fucosidase in transglycosylation reaction, a mixture of donor sugar 3 (20 mM), acceptor sugar (4) (10 mM) and enzyme AlfC E274G (0.2 mg/mL) was incubated in a PBS buffer (0.1 M, pH7.5) containing 5% DMSO. The reactions were carried out for 20 min at various temperatures, including 25° C., 30° C., 35° C., 40° C., 45° C., 50° C. and 55° C. The transglycosylation product was quantitated by HPLC analysis.

Interestingly, it was observed that in the absence of the GlcNAc acceptor, the AlfC mutants (E274A, E274G, and E274S) only hydrolyzed α-fucosyl fluoride slowly but the wild type AlfC could quickly hydrolyze the donor substrate. Taken together, these results indicated that the AlfC mutants represented a class of unique O-fucoligase for core-fucosylation, which could use synthetic α-fucosyl fluoride as the simple donor substrate instead of the expensive GDP-fucose as the substrate in the case of α-fucosyltransferase. To examine whether the fused CPD domain in the enzyme played a role in catalyzing fucosylation, the CPD tag was removed in the AlfC E274A mutant by using inositol hexaphosphate (FIG. 13). The purified mutant without CPD tag showed comparable catalytic activity as its CPD tagged counterpart, indicating that CPD tag did not affect the catalytic activity of the mutant (Data not shown). However, it was found that the mutants fused with the CPD were more thermostable than the free enzyme. While incubation of the free enzyme at 55° C. for 5 h led to partial precipitation probably due to aggregation, the CPD fused mutant was still active, indicating that the CPD domain could stabilize the enzyme. A detailed study on the fucosylation activity of E274A indicated that the optimal pH of its catalysis was 7-8.5 and the optimal temperature was 40-50° C. (FIG. 14).

Figure 15:
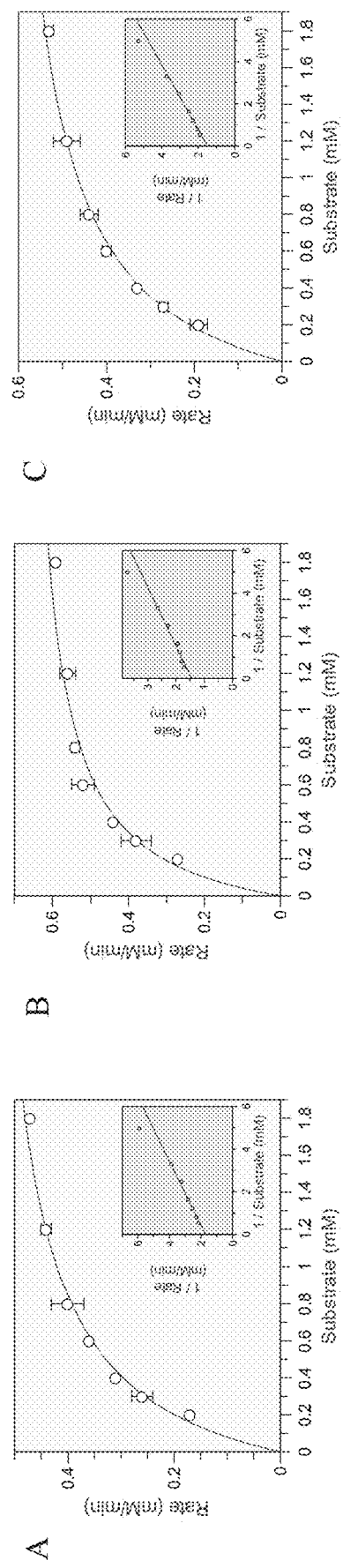
FIG. 15 shows Michelis-Menten plots for transglycosylation kinetics of AlfC mutant E274G (A), E274A (B) and E274S (C).

Kinetic studies were also performed on the mutants and the results were summarized in Table 2 and FIG. 15. The E274A mutant exhibited the highest transfucosylation activity with catalytic efficiency ($k_{cat}/K_M$) of up to $1.6×10^3$ min$^{-1}$ mM$^{-1}$ and E274S and E274G also showed high activities (Table 2). In particular, kinetic analysis revealed that these mutants had high turnover numbers ($k_{cat}$>200 min$^{-1}$) implying that these mutants, with mutation at the general acid/base residue, could efficiently use the α-fucosyl fluoride for transglycosylation without hydrolysis of the product.

Direct Core-Fucosylation of Various GlcNAc-Peptides.

The discovery that the E274A and related mutants were able to efficiently catalyze the trans-fucosylation on the GlcNAc-Asn derivative prompted us to test if the mutants could also fucosylate GlcNAc moiety in the context of polypeptides. Three distinct GlcNAc-containing peptides were chosen for the test: the hexapeptide (6) derived from the sialylglycopeptide (SGP) isolated from egg yolks, a 19-mer GlcNAc-peptide (8) that consisting of the CD52 antigen and a sortase A signal peptide sequence, and a potent HIV inhibitor GlcNAc-C34 (10) derived from the HIV-1 gp41 envelope glycoprotein[70].

Figure 4:
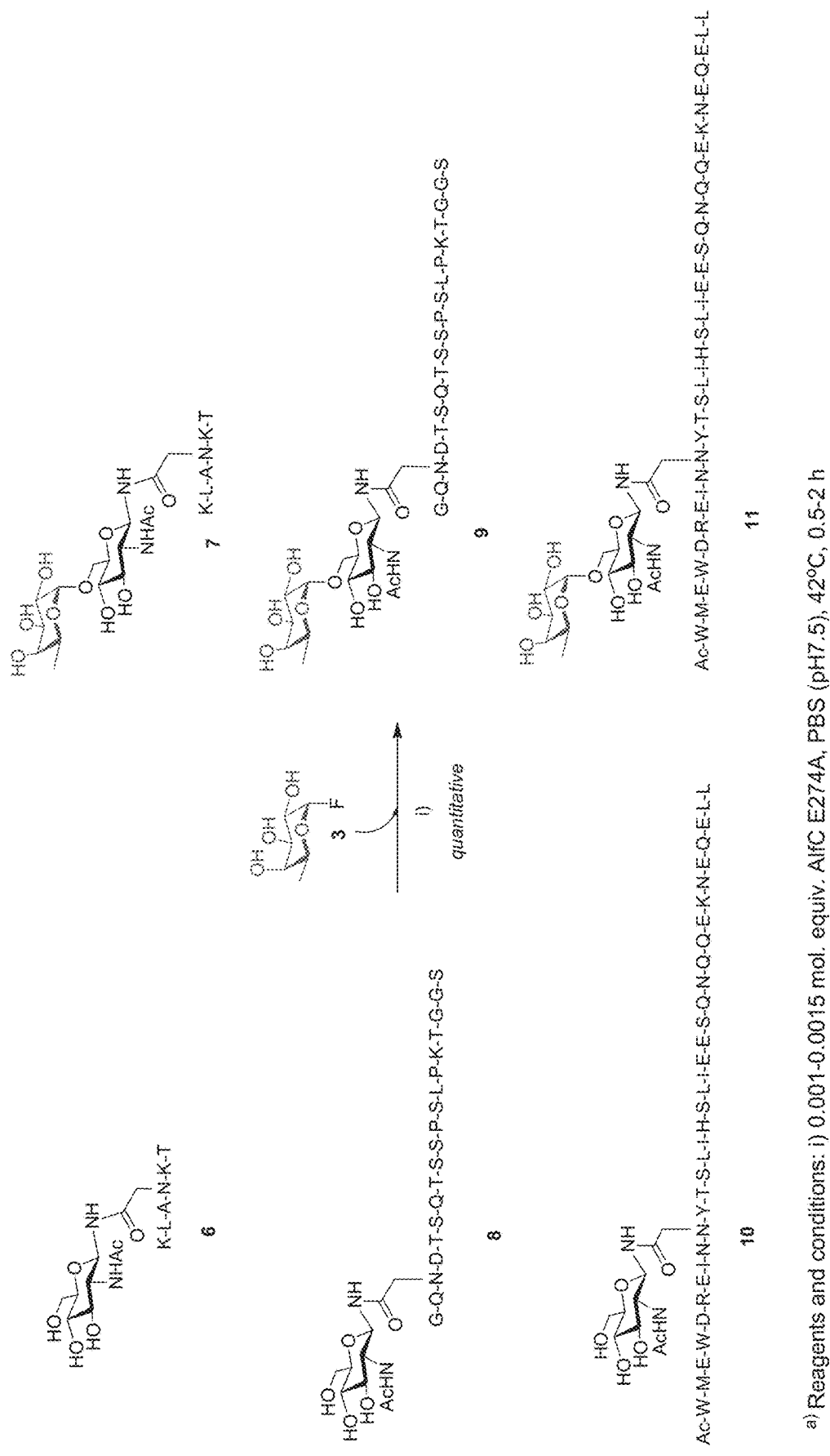
FIG. 4 shows core fucosylation of GlcNAc-peptides by the fucoligase. Peptide Structure 6 and 7 (SEQ ID NO:10), peptide structure 8 and 9 (SEQ ID NO: 11) and peptide structure 10 and 11 (SEQ ID NO: 12).
Figure 16:
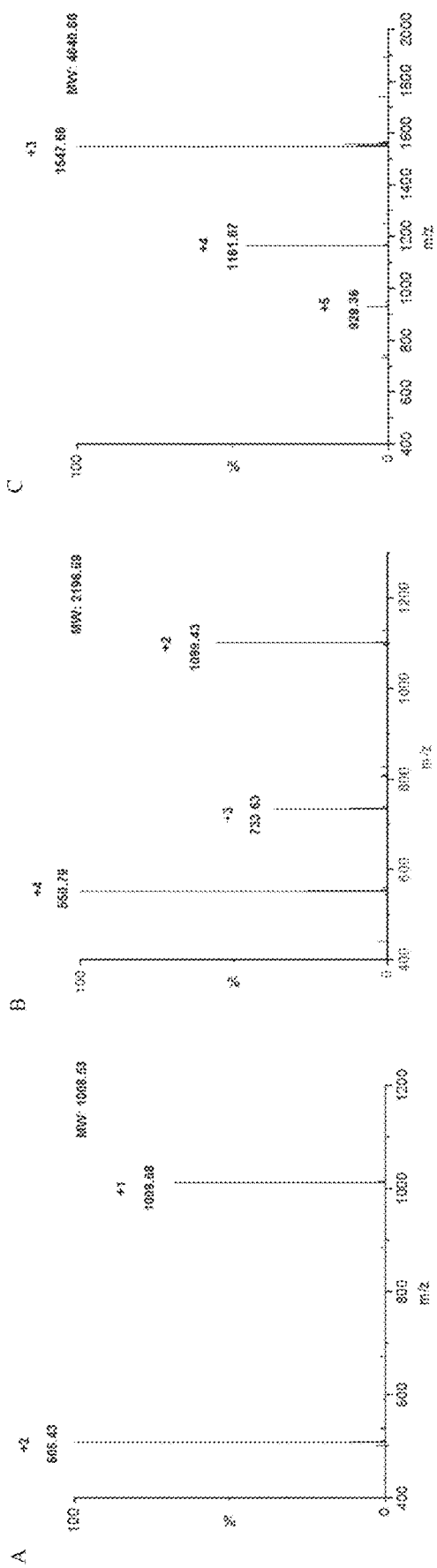
FIG. 16 shows the ESI-MS spectra of fucosylated peptides. Products 7 (A), 9 (B) and 11 (C).

It was found that the E274A could transfer a fucose moiety to all the three GlcNAc-peptides to form the corresponding fucosylated peptides (7, 9, and 11), respectively (FIG. 4). While the small GlcNAc-peptide (6) was transformed faster than the large ones (8 and 10), all the enzymatic fucosylation could be achieved essentially quantitatively within a relatively short time of incubation (1-2 h) when a sufficient amount of enzyme was used. The glycopeptide products were readily purified and its identity was confirmed by LC-MS analysis (FIG. 16). The Fucα 1,6GlcNAc-peptides could serve as excellent acceptor substrates for the Endo-F3 D165A glycosynthase to synthesize core-fucosylated complex N-glycopeptides[66].

Direct Core Fucosylation of Intact N-Glycopeptides.

Figure 5:
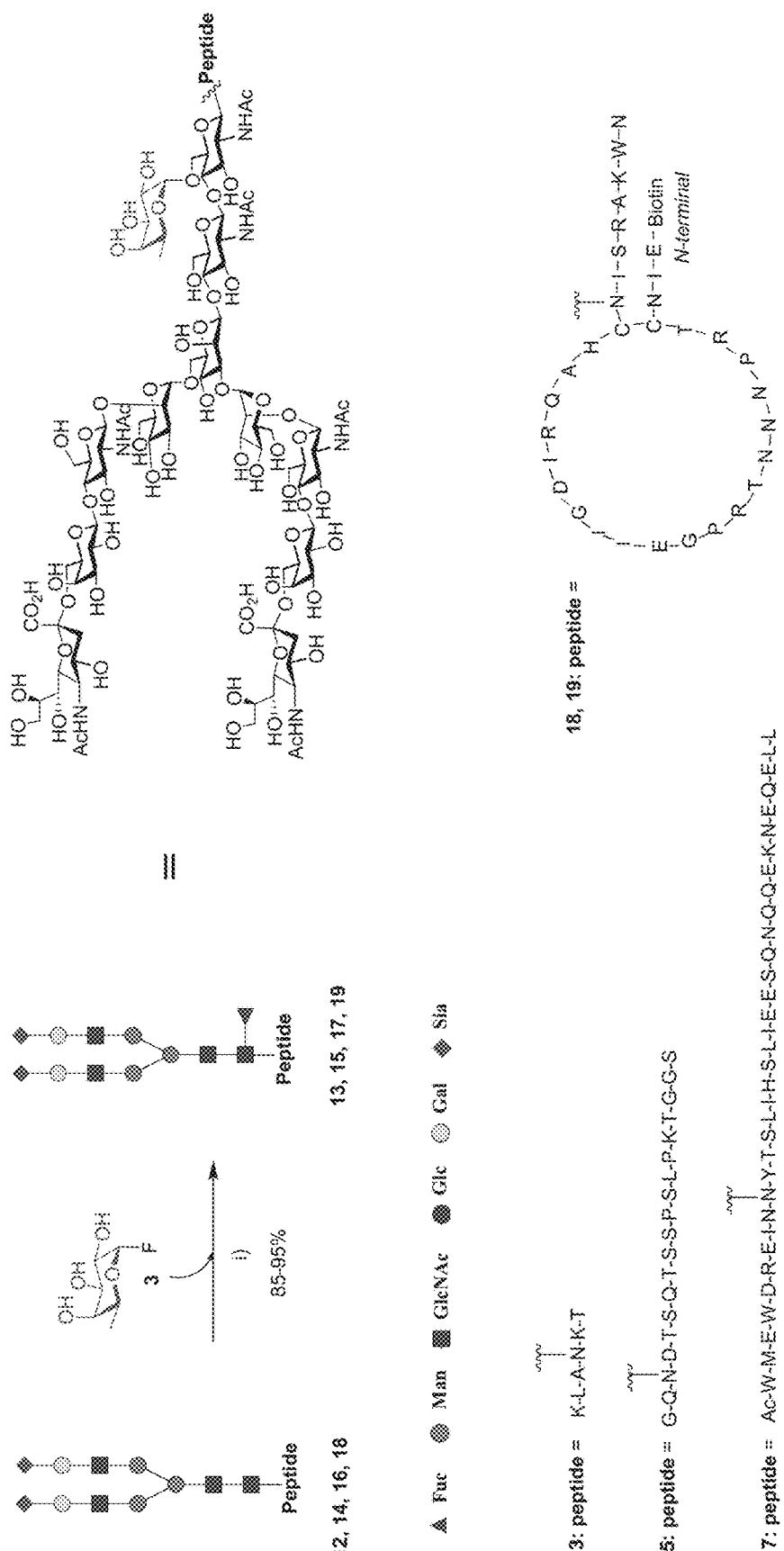
FIG. 5 shows fucoligase catalyzed direct core fucosylation of intact N-glycopeptides. Peptide structure 12 and 13 (SEQ ID NO 10), peptide structure 15 and 16 (SEQ ID NO: 11), peptide structure 16 and 17 (SEQ ID NO: 12) and peptide structure 18 and 18 (SEQ ID NO.
Figure 17:
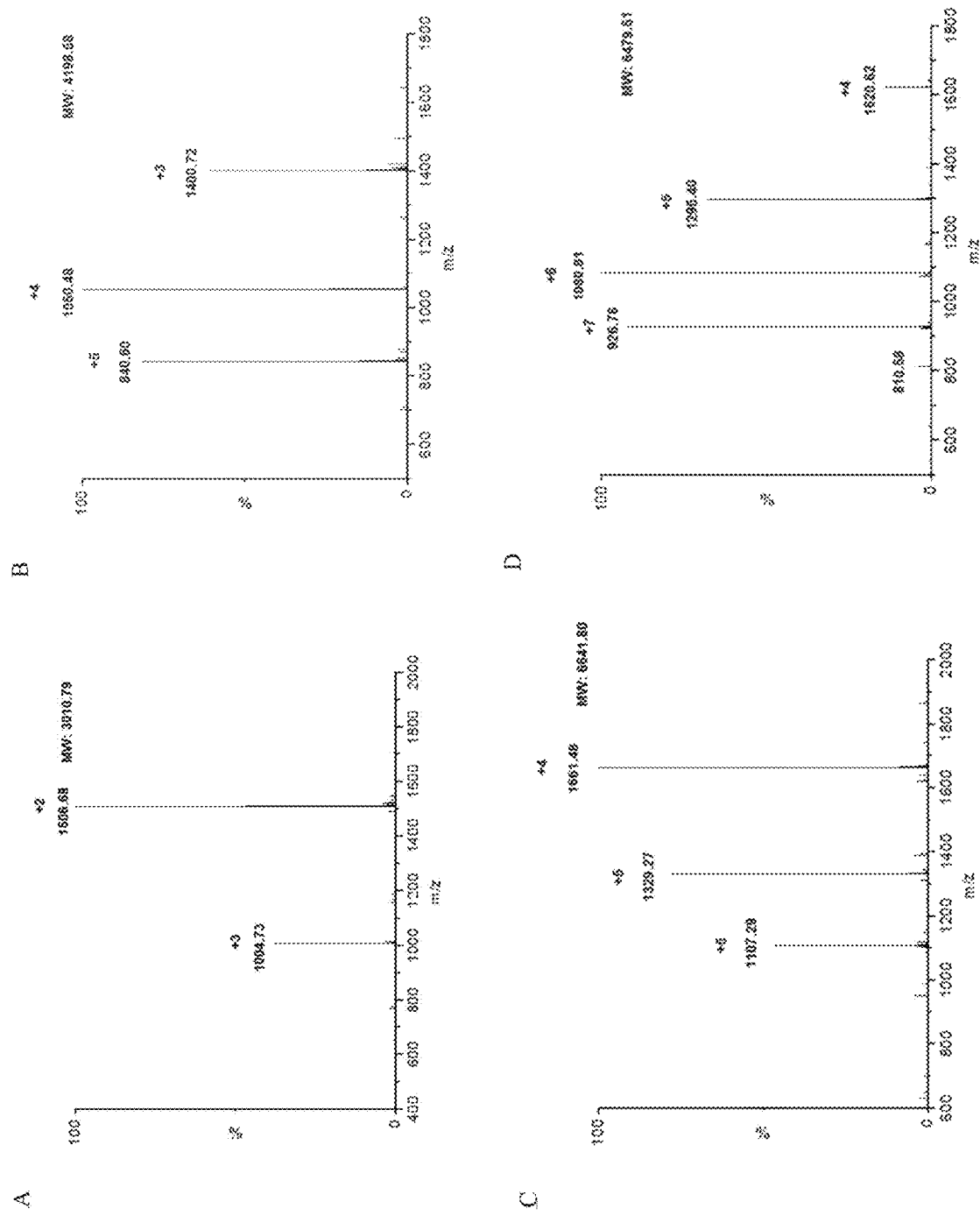
FIG. 17 shows the ESI-MS spectra of core fucosylated glycopeptides. Products 13 (A), 15 (B), 17 (C) 19 (D).

Next, the feasibility was tested of E274A-catalyzed directed core-fucosylation of intact N-glycopeptides carrying a full-size N-glycan. Several complex N-glycopeptides (12, 14, 16, and 18) carrying a sialylated biantennary complex type N-glycan were used as potential acceptor substrates, including a large cyclic HIV-1 V3 glycopeptide (18). Surprisingly, the E274 mutant could efficiently add a core fucose to the intact N-glycopeptides to give the corresponding core-fucosylated N-glycopeptides (13, 15, 17, and 19), respectively in excellent yields (FIG. 5). The glycopeptide products were separated by RP-HPLC and their identities were first characterized by ESI-MS analysis (FIG. 17).

Figure 18:
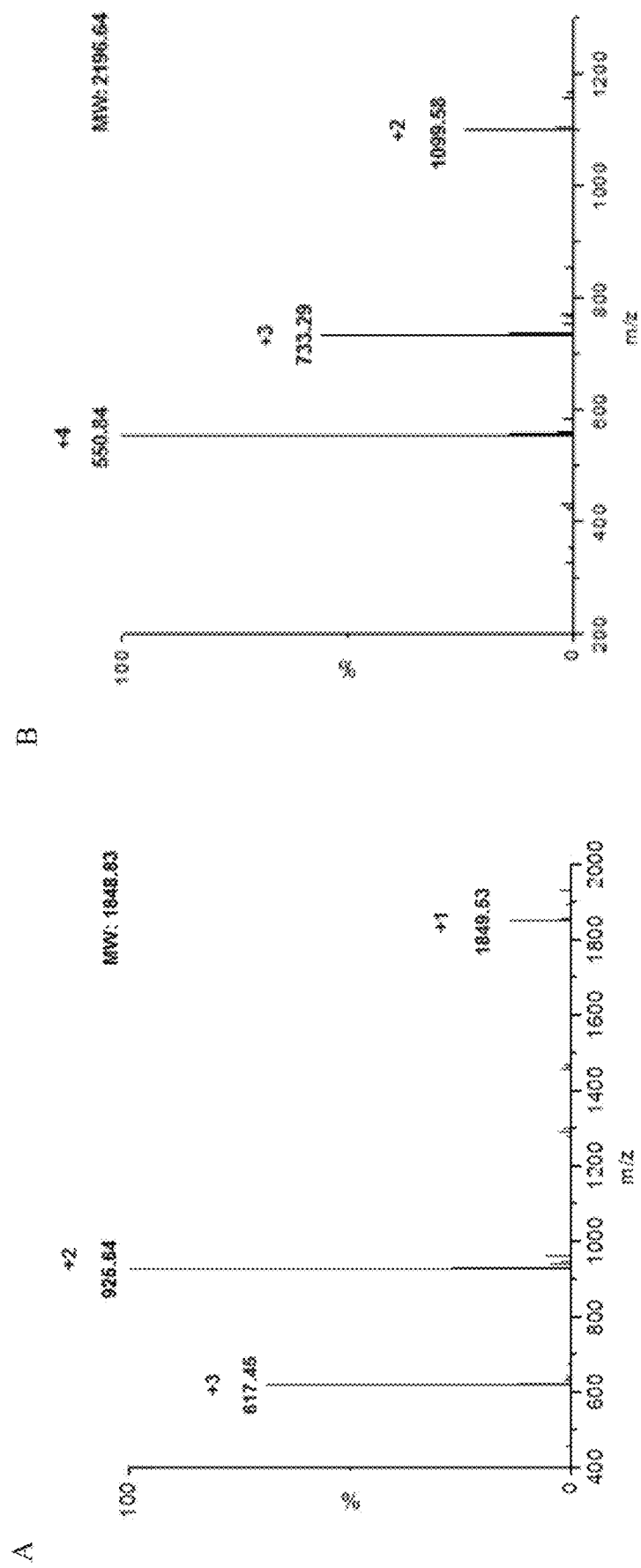
FIG. 18 shows the characterization of 15 by enzymatic transformation coupled with ESI-MS analysis. A) the ESI-MS of the product from the PNGase F treatment of 15; B) the ESI-MS of the product from the Endo-F3 treatment of 15.

To verify that the fucose was specifically added to the innermost GlcNAc moiety in the glycopeptide, the isolated glycopeptide product (15) was treated with two specific hydrolytic enzymes PNGase F and Endo-F3 that hydrolyze N-glycopeptides and N-glycoproteins. PNGase F completely removes the N-glycans from N-glycopeptides by hydrolyzing the amide linkage between asparagine and the N-glycans, while Endo-F3 specifically cleaves at the β1,4-glycosidic bond between the two GlcNAc moieties in N-glycopeptides/proteins. ESI-MS analysis indicated that treatment of 15 with PNGase F efficiently converted 15 into a single peptide species that was corresponding to the free polypeptide without any sugar attached (Calcd for the plain polypeptide, M=1848.75 Da; found, M=1848.83 Da) (FIG. 18A), suggesting that the fucose must be transferred to the N-glycan portion instead of any residues on the peptide portion. On the other hand, treatment of 15 with Endo-F3 gave a species that corresponded to Fucα1,6GlcNAc-peptide (9) (ESI-MS, calculated, M=2195.38 Da; found, M=2196.64 Da, deconvolution data) (FIG. 18B). Taken together, these experimental data suggested that indeed the fucose moiety was added specifically to the innermost, Asn-linked GlcNAc moiety of the glycopeptide in the glycoligase-catalyzed fucosylation. The ability to directly core-fucosylated intact N-glycopeptides opens a new avenue to access core-fucosylated N-glycopeptides directly from natural and synthetic N-glycopeptides.

Direct Core Fucosylation of Intact Glycoproteins.

Figure 19:
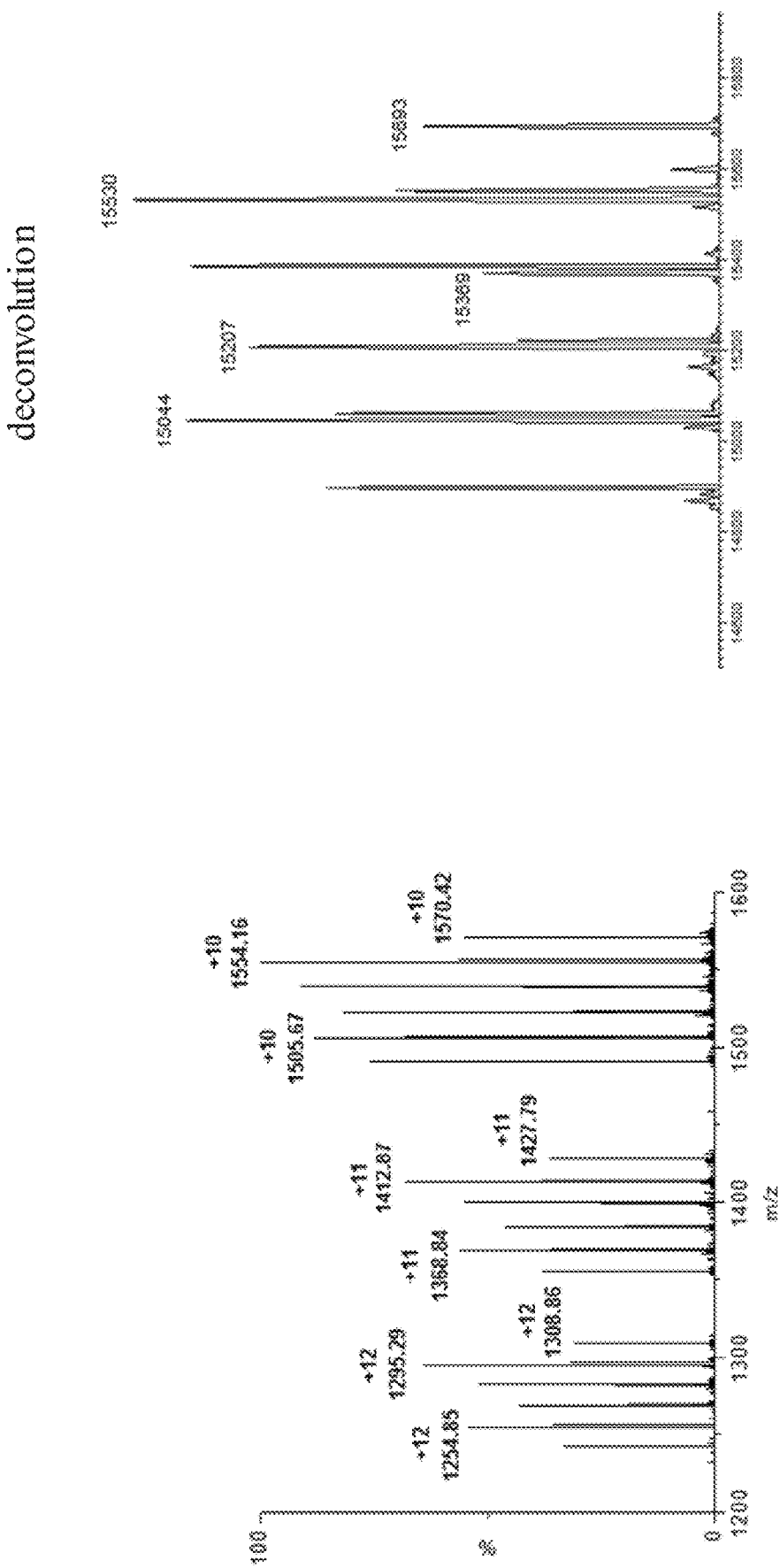
FIG. 19 shows the characterization of mixture of the product (21) and the substrate (20). ESI-MS spectrum of the mixture and the corresponding deconvolution.
Figure 20:
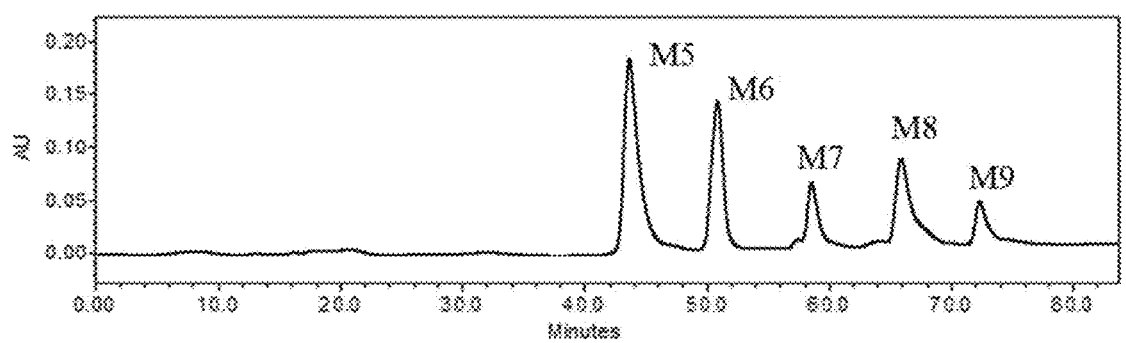
FIG. 20 shows HPLC chromatography of Fmoc-labeling glycans of RNase B. A) Fmoc tagged N-Glycans from RNAse B 20. B) Fmoc tagged N-Glycans from the transglycosylation mixtures containing the starting glycoprotein (20) and the fucosylated RNase B (21).
Figure 20:
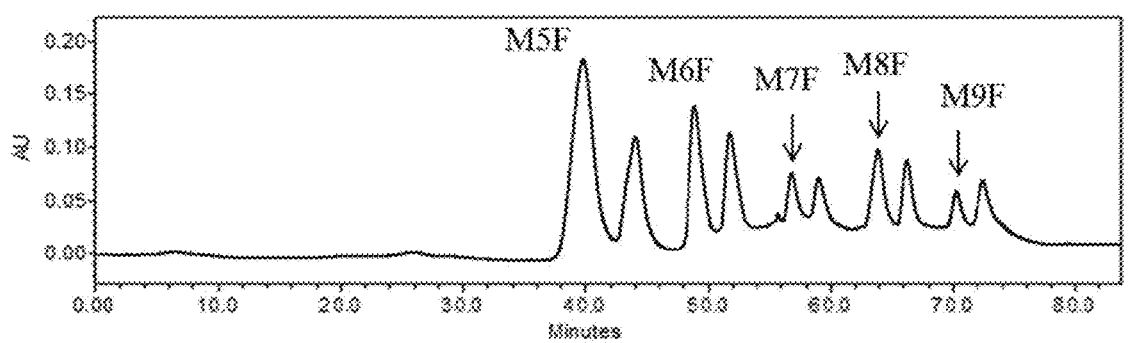

The success in direct core-fucosylation intact glycopeptides by the glycoligase mutants encouraged us to also test the direct core-fucosylation of intact N-glycoproteins. Thus, bovine ribonuclease B (RNase B, 20) was chosen, a natural glycoprotein with heterogeneous high-mannose type N-glycan, as a model system to investigate whether this engineered enzyme was capable of fucosylating the natural glycoprotein. RNase B is a good model for the study of protein glyco-remodeling, as it has only a single N-glycosylation site, N34, located around the cleft of the spheroidal protein. The N-glycans on natural RNase B are a mixture of high mannose type from five to nine mannose residues. Firstly, it was examined whether the E274A mutant could perform direct core-fucosylation on the glycoform mixtures and, if yes, whether the mutant showed any selectivity on the N-glycans of different size. Thus, RNase B (20) was incubated with 3 and the E274A mutant at 37° C. (a lower temperature to prevent protein denaturation). The reaction was monitored with LC-MS. To calculate the reaction yields, glycans were cleaved from the protein with PNGase F and then detected and quantitated with HPLC after Fmoc-labelling (See experimental section)[71]. It was found that RNase B (20) could serve as an acceptor substrate of AlfC E274A for core-fucosylation (FIG. 6), but the reaction was relatively slow, giving partial transformations to the fuocsylated RNase B glycoforms 21 under the conditions after 5 h (FIG. 19). Interestingly, the E274A mutant exhibited some substrate specificity on the different glycoforms. The yields of core fucosylation of respective glycoforms, as judged by the HPLC analysis of the released core-fucosylated N-glycans were 72%, 54%, 51%, 55% and 43%, for the Man5 to Man9 glycoforms, respectively (FIG. 20). These results suggested that for high-mannose type N-glycoforms, the larger size N-glycans were less favorable substrate for E274A, probably due to steric hindrance. This study also demonstrated that high-mannose type glycoproteins could serve as substrates for core-fucosylation by the fucoligase mutant.

Figure 6:
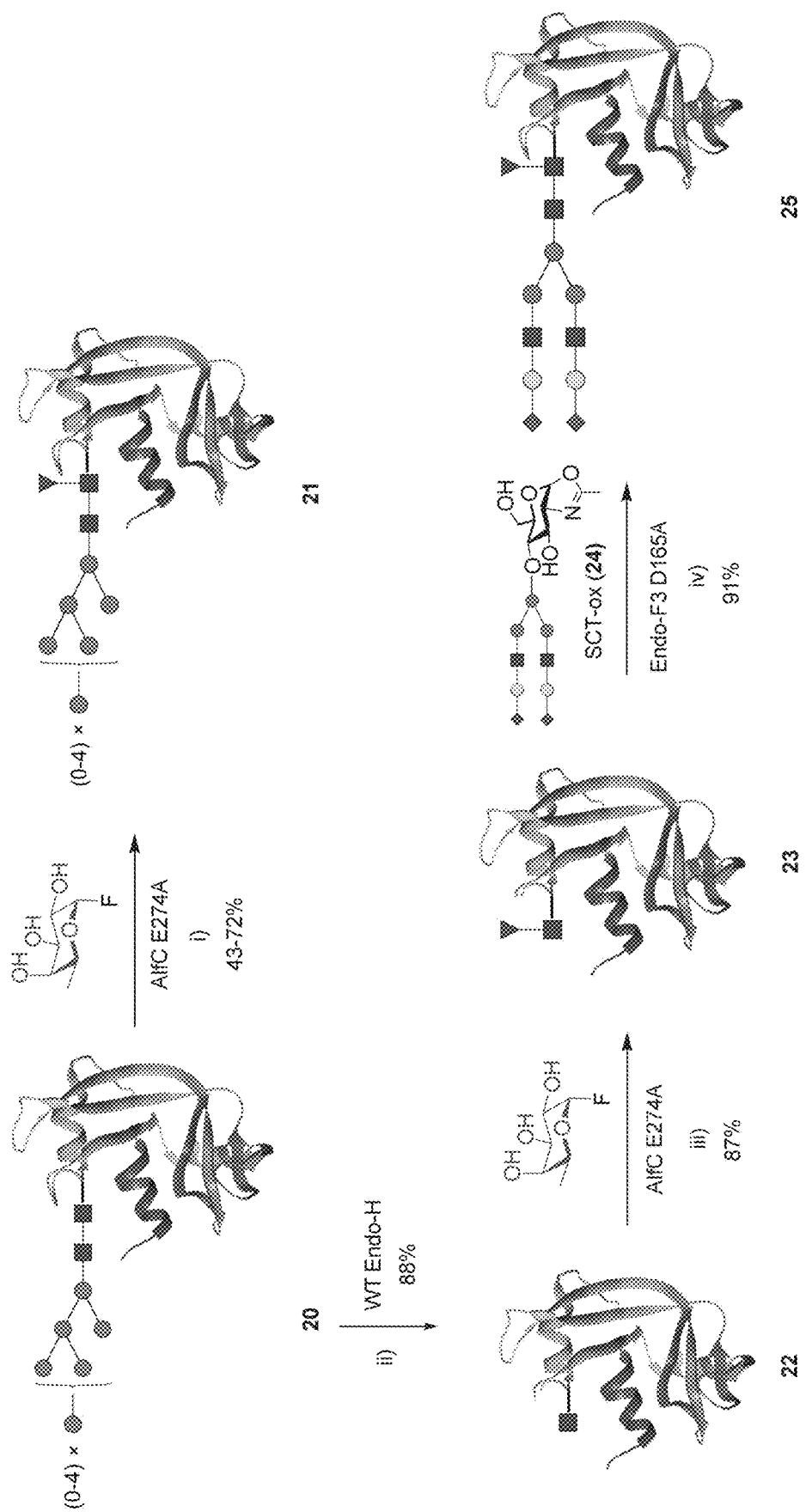
FIG. 6 shows fucoligase mediated glycol-remodeling of natural glycoprotein RNase.
Figure 21:
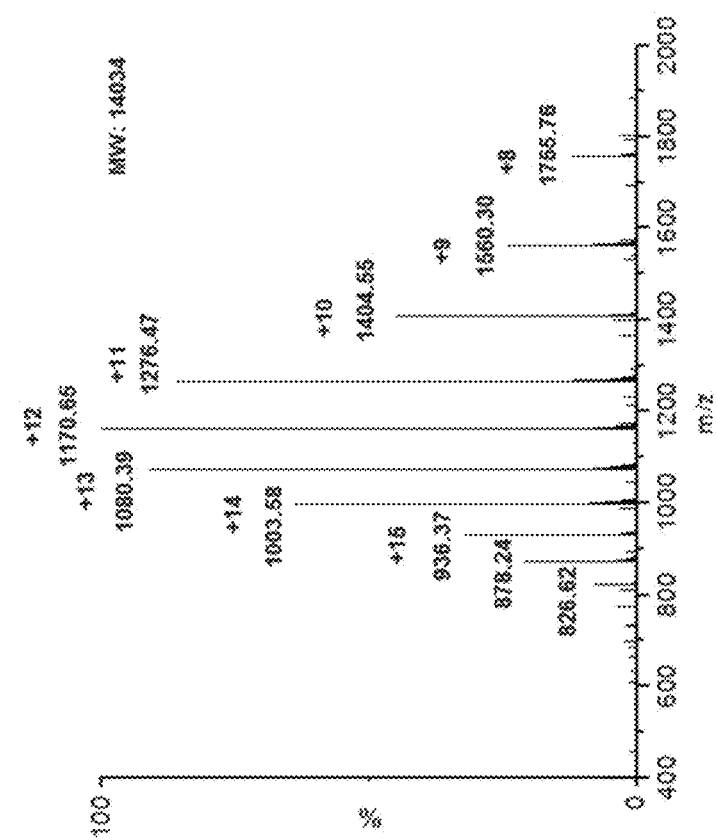
FIGS. 21 A and B show the characterization of RNase derivatives (23 and 25).
Figure 21B:
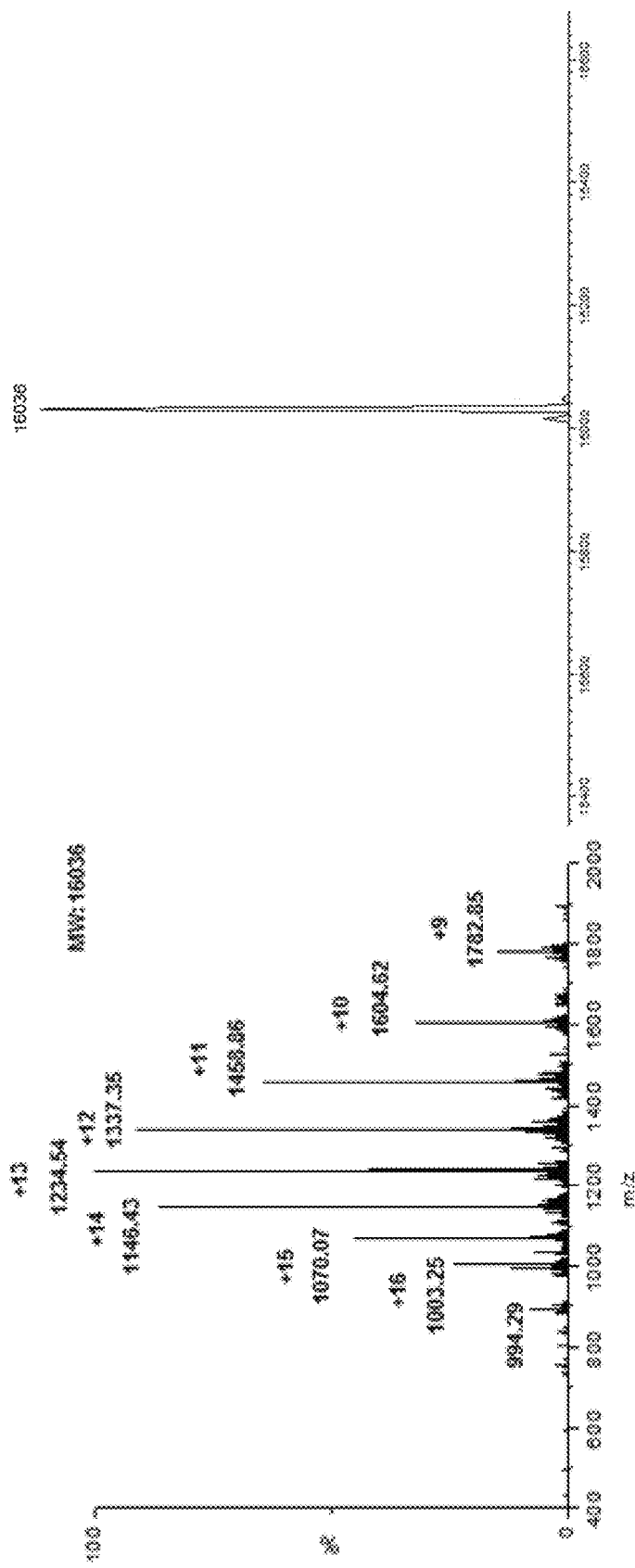

Since the direct core-fucosylation of RNase B was less efficient, an alternative approach was tested that consists of deglycosylation, glycoligase-catalyzed core-fucosylation, and Endo-F3 catalyzed transglycosylation to constitute a core-fucosylated complex type RNase glycoform (Ribonuclease C) (FIG. 6). Thus, The high mannose N-glycans in RNase B (20) was removed by Endo-H to afford the deglycosylated protein GlcNAc-RNase (22) in quantitative yield[72]. It was found that, in contrast to the slow fucosylation of the intact RNase B (20), the core fucosylation of GlcNAc-RNase (22) was much more efficient to give the Fucα1,6GlcNAc-RNase (23) in essentially quantitative yield within 5 h under the same conditions. Deconvolution of the ESI-MS spectrum gave a single species confirming the identity of the fucosylated product (Calculated for 23, M=14031 Da; found, M=14034 Da) (FIG. 21A). Subsequently, Endo-F3 D165A catalyzed glycosylation of the Fucα1,6GlcNAc-RNase (23) with a complex glycan oxazoline (24), following a previously reported procedure by the present inventor, gave the core fucosylated complex glyvoform (25) in 97% yield (FIG. 6). ESI-MS analysis verified the glycosylation product (Calculated for 25, M=16033 Da; found, M=16036 Da) (FIG. 21B). This was the first synthesis of core-fucosylated complex type glycoform of RNase (RNase C). The synthesis was more efficient than the preparation of the non-fucosylated RNase C that was previously reported using Endo-M mutant for transglycosylation[73]. The ability of the fucoligase mutant to directly fucosylate intact glycopeptides and glycoproteins significantly expands the repertoire of toolkits for making homogeneous core fucosylated glycoforms for various glycomic applications.

Direct Enzymatic Core-Fucosylation of Intact Monoclonal Therapeutic Antibody.

Figure 7:
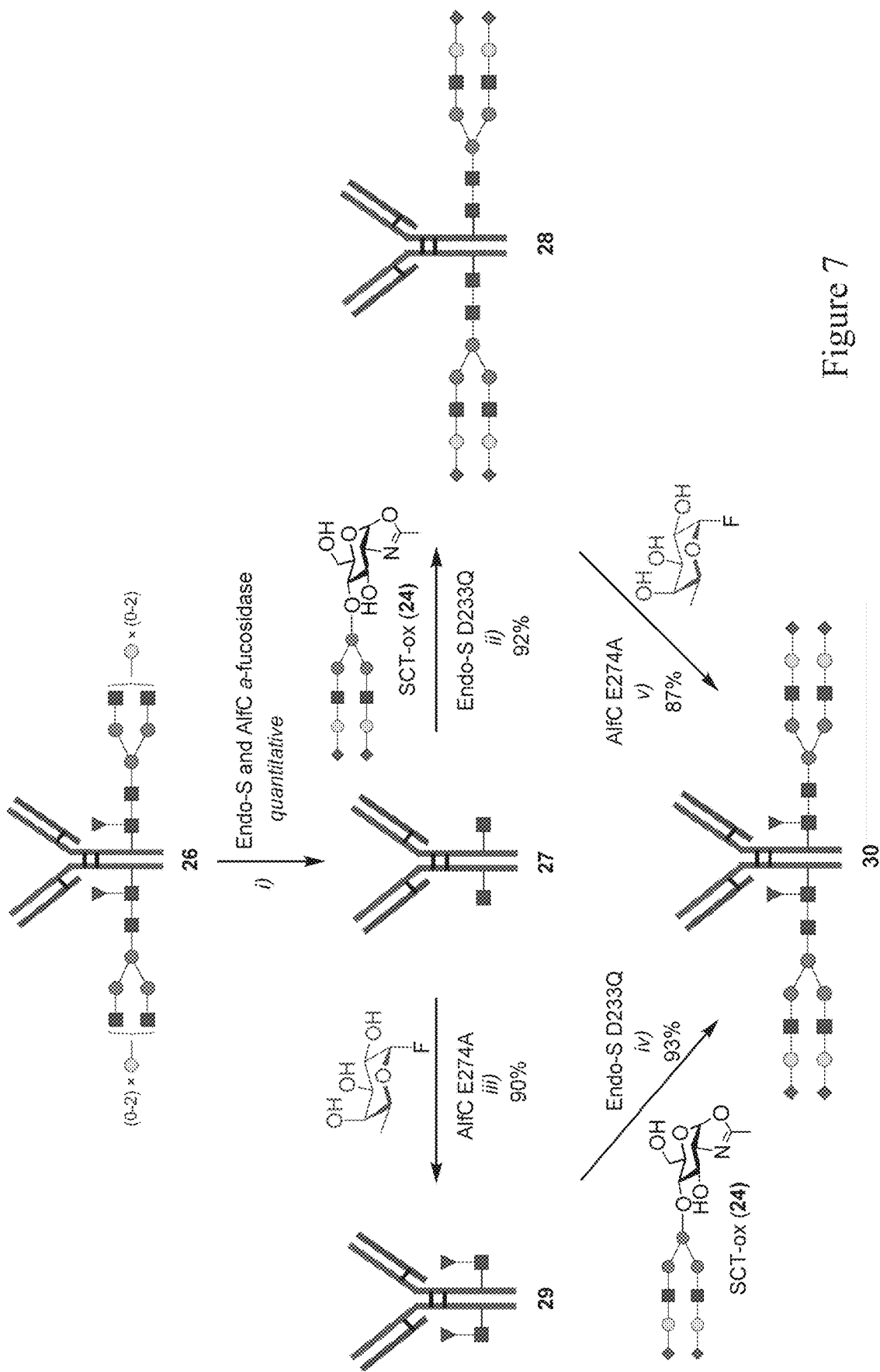
FIG. 7 shows chemoenzymatic glycoengineering of human IgG combined with fucoligase promoted core fucosylation. Reagents and conditions: i) AlfC E274A (0.042 mol. equiv. of 20), PBS (pH 7.5), 42° C., 5 h; ii) Endo-H (0.01 mol. equiv. of 20), PBS (pH6.0), 37° C., 1.5 h; iii) AlfC E274A (0.021 mol. equiv. of 22), PBS (pH 7.5), 42° C., 6 h; iv) Endo-F3 D126A (0.015 mol. equiv. of 23), PBS (pH6.5), 37° C., 0.5 h.
Figure 22:
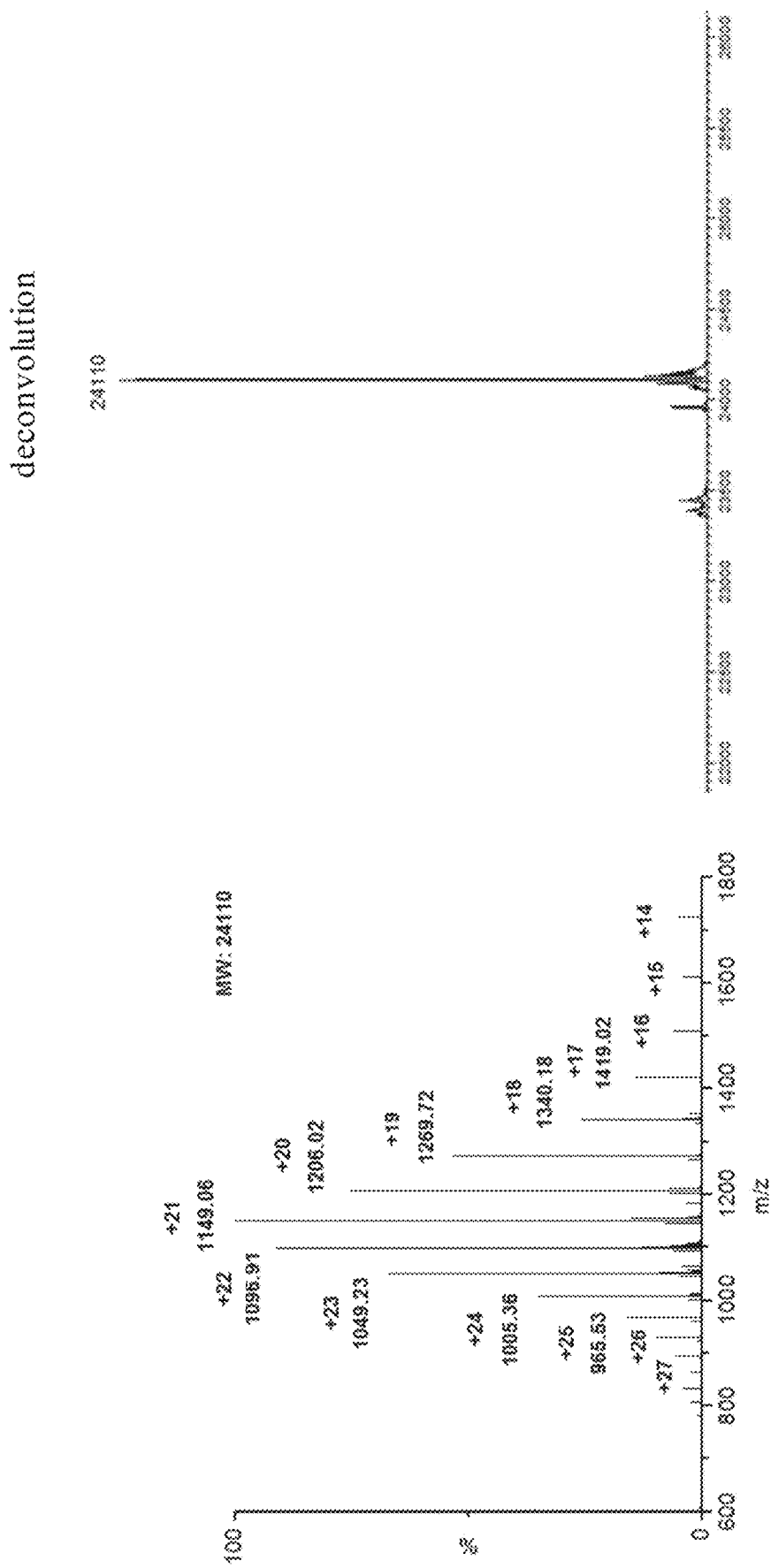
FIG. 22 shows the ESI-MS of the Fc domain from the IdeS treatment of 29 and the corresponding deconvolution.

The potent transfucosylation activity of AlfC α-fucoligase towards glycopeptides and glycoproteins prompted further exploring of its application for glycoengineering of therapeutic monoclonal antibodies. Core fucosylation of the Fc domain N-glycans plays a pivotal role in modulating the functions of antibodies and their therapeutic efficacy[8,74]. It was previously developed by the current inventors a chemoenzymatic Fc glycan remodeling method that consists of deglycosylation and glycosynthase-catalyzed glycan transfer to produce homogeneous Fc glycoforms[65,66,75]. If the fucoligase mutant could act on intact antibody, then it would further expand the repertoire of the toolbox for antibody Fc glycan engineering. To test this possibility, rituximab (26) was selected as a model system. First, rituximab was deglycosylated with Endo-S followed by defucosylation with the wild type AlfC α-fucosidase to give the GlcNAc-rituximab (27) (FIG. 7). Interestingly, wild-type AlfC α-fucosidase showed good hydrolytic activity, to afford the deglycosylated product (27) with essentially complete transformation within 3 h. However, it was found that wild-type AlfC α-fucosidase was unable to remove the fucose moiety in the intact rituximab before Endo-S treatment, even with significantly large amount of the enzyme and prolonged incubation time (data not shown). The non-fucosylated complex type glycoform (28) of rituximab was synthesized by the EndoS-D233Q catalyzed glycosylation with glycan oxazoline (24) as the donor, following previously published procedure[75]. These two glycoforms (27 and 28) were used as potential substrates for examining the AlfC fucoligase mutants. The GlcNAc-rituximab (27) was incubated with α-fucosyl fluoride (3) and AlfC E274A mutant at 37° C. and the reaction was monitored by LC-MS analysis. It was found that GlcNAc-rituximab acted as an excellent substrate of the fucoligase AlfC E274A and the enzymatic reaction resulted in complete core-fucosylation of 27 to give the Fucα1,6GlcNAc-rituximab (29) as a single product within 6 h under the conditions. The product was readily isolated by protein A affinity chromatography. To confirm the identity of the Fucα1,6GlcNAc-rituximab (29), the product was treated with protease IdeS which specifically hydrolyzes IgG antibody to release the monomeric Fc domain, and the released Fc was analyzed by ESI-MS. The deconvolution of the ESI-MS of core fucosylated Fc domain exhibited a single species with the expected molecular mass (Calculated for Fucα1,6GlcNAc-Fc, M=24112 Da; found, M=24110 Da) (FIG. 22). The 146 Da increase from 27 to 29 suggested an addition of a single fucose moiety in the monomeric Fc domain. As described previously, Fucα1,6GlcNAc-rituximab (29) was an excellent substrate for EndoS-D233Q[75]. Indeed, incubation of 29 with EndoS-D233Q and glycan oxazoline (24) gave the expected core-fucosylated complex type glycoform of rituximab (30) in excellent yield, further confirming that the 29 was the expected Fucα1,6GlcNAc-rituximab.

Finally, the direct fucosylation of the intact rituximab (28) was tested carrying the full size complex type Fc N-glycans. Interestingly, it was found that the AlfC E274 mutant could also smoothly transfer the fucose moiety to the intact rituximab, albert at a slow rate in comparison with the GlcNAc-rituximab substrate. Nevertheless, an increased amount of the enzyme could lead to complete transformation of the intact rituximab (28) to the core-fucosylated glycoform (30) within a few hours at 37° C. (FIG. 7). This result is remarkable given the fact that the Fc domain N-glycans are buried between two Fc domains, and that wild type AlfC α-fucosidase actually shows almost no activity to remove the core fucose in the intact Fc N-glycans. It is puzzling why the wild type α-fucosidase was unable to hydrolyze the fucose in the intact antibody but the E274A mutant could manage to access the site to efficiently perform the trans-fucosylation on the intact antibody.

Figure 8:
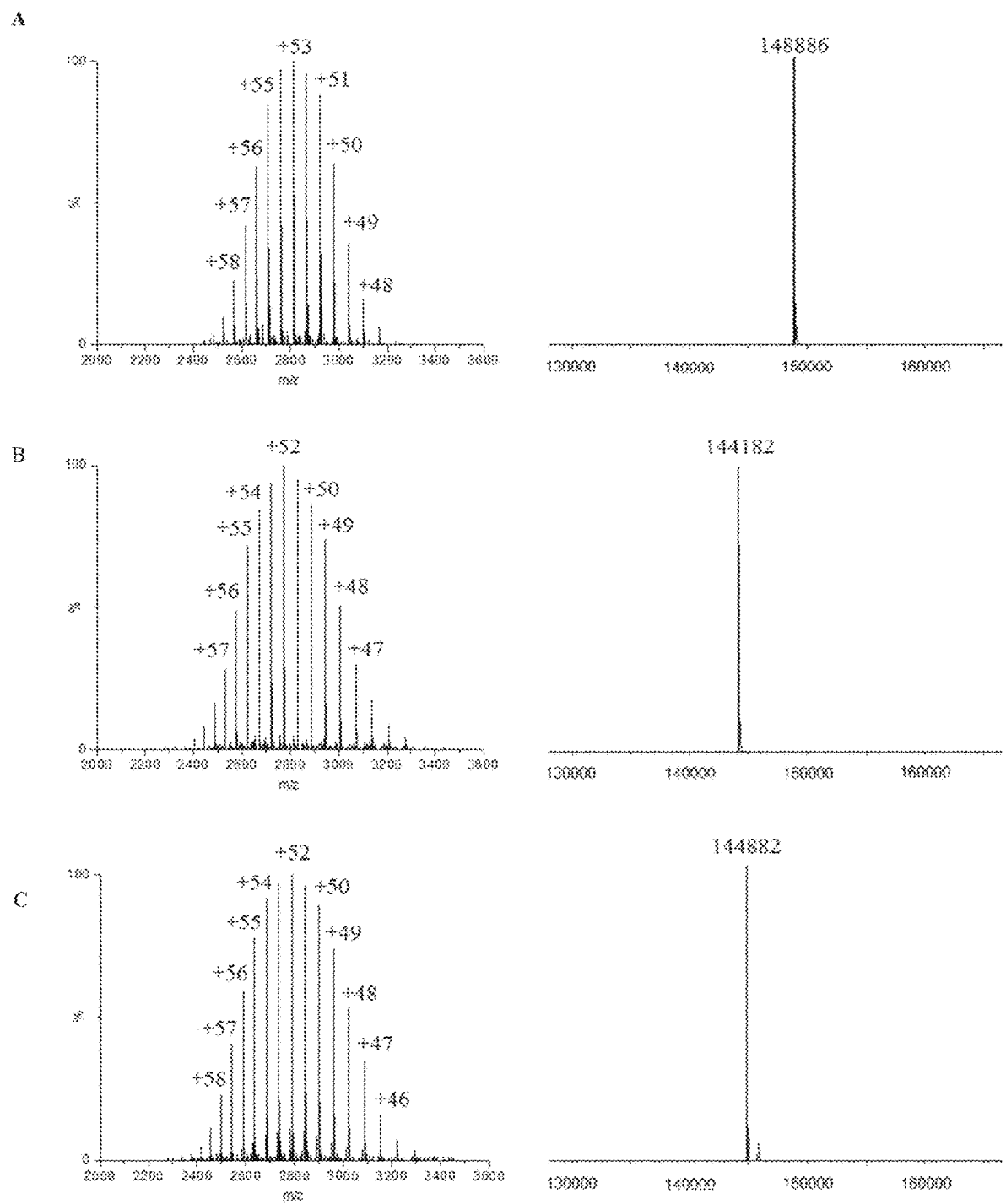
FIG. 8 show the characterization of the fucosylated rituximab (30). A) ESI-MS spectrum and its deconvolution of 30; B) ESI-MS spectrum and its deconvolution of the product from the PNGase F treatment of 30; C) ESI-MS spectrum and its deconvolution of the product from the Endo-S treatment of 30.

To confirm that the fucose was specifically attached at the core position and that there was no non-enzymatic attachment of the fucose to any residues in the protein portions, ESI-MS analysis was performed of the intact antibody product, coupled with specific enzymatic transformations (FIG. 8). First, the observed molecular mass of 30 from the ESI-MS deconvolution data matched well the expected molecular mass (Calcd, M=148888 Da, found, M=148886 Da) (FIG. 8A). The data suggested an addition of two fucose moieties on top of the intact rituximab (28) that was a dimer carrying two N-glycans (each heavy chain has an N-glycan at the Asn-297 site); second, PNGase F treatment of 30 gave a single species of the antibody, the ESI-MS deconvolution data (144182 Da) of which agreed with the polypeptide backbone of rituximab (calcd, M=144181 Da) (FIG. 8B). This result suggested that there was no any additional modification of the protein portions of rituximab during the AlfC E274A catalyzed reactions; Third, Endo-S treatment of 30 converted it back to the Fucα1,6GlcNAc-rituximab (29), which appeared as a single species at 144882 Da (FIG. 8C).

Lectin Binding Studies with Core-Fucosylated RNase B and Rituximab.

Figure 9:
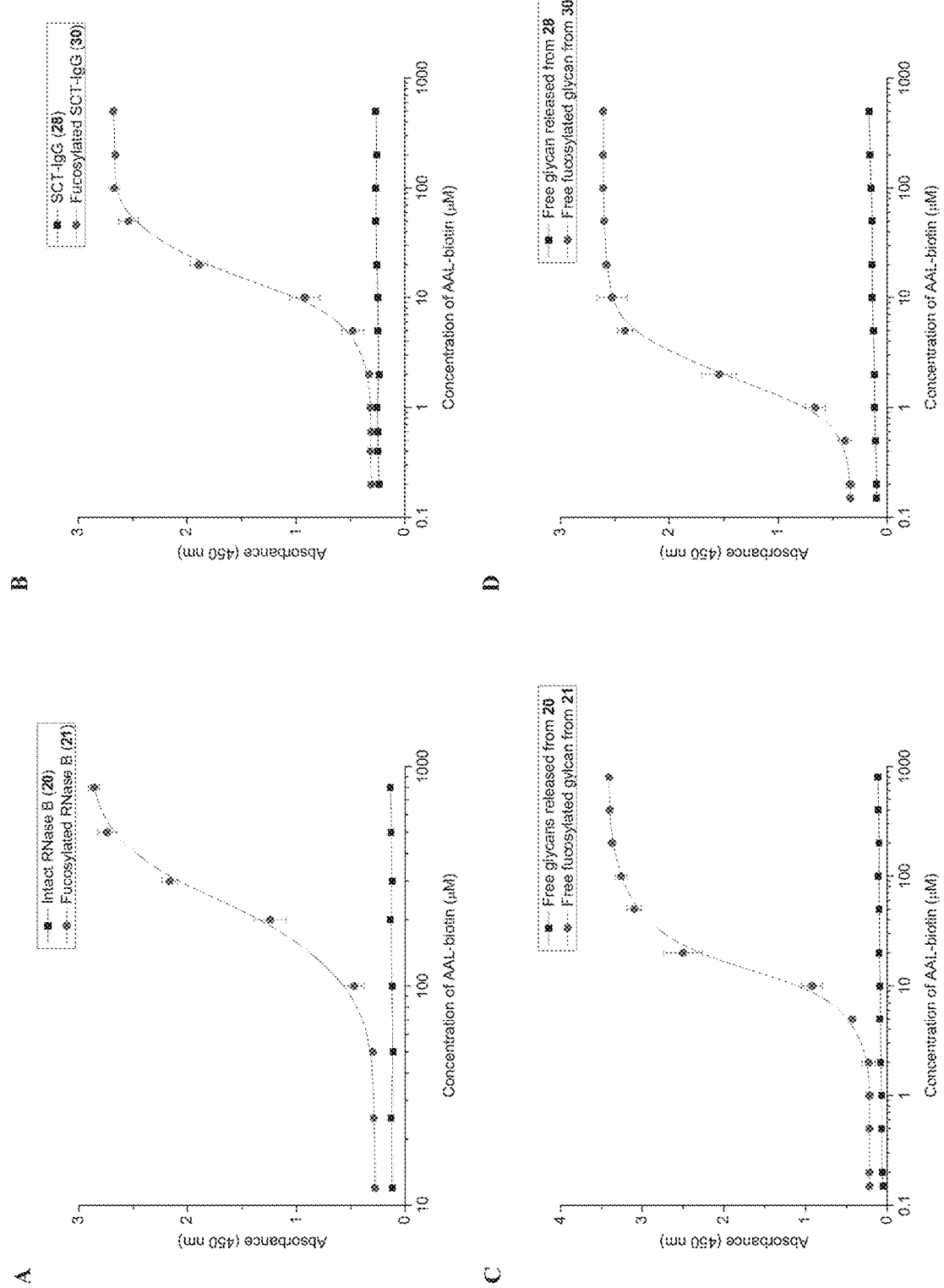
FIG. 9 ELISA analysis of the binding between lectin AAL and glycoproteins or released N-glycans. The glycoproteins or released N-glycans (tagged with Fmoc) were immobilized on the plates and probed by serial dilutions of the lectin. A) AAL binding with RNase B (20) and fucosylated RNase B (21); B) AAL binding with non-fucosylated glycoform of rituximab (28) and fucosylated rituximab glycoform (30); C) AAL binding with the PNGase F released high-mannose N-glycans released from 20 and 21; D) ALL binding with the PNGase F released complex type N-glycans from 28 and 30.

The interactions of glycoproteins and core fucose-specific lectins play important roles in biological recognition processes. To demonstrate the specific recognition, the binding analysis of the interactions between the *Aleuria aurantia* lectin (AAL) and a few core-fucosylated glycoproteins synthesized via the AlfC fucoligase catalyzed reactions was performed. AAL is a commonly used lectin, which has high affinity for α1,6-fucosylated glycoproteins, including core fucosylated antibody and haptoglobin[76,77]. First the binding of 21 carrying core fucosylated high-mannose glycans and the natural glycoprotein (20) with AAL was tested. The AAL showed specific binding to 21, while it didn't show any binding to the non-fucosylated glycoprotein (20) (FIG. 9A). AAL also demonstrated specific recognition of the core fucosylated antibody (30) but did not show any detectable affinity to the non-fucosylated antibody (28) (FIG. 9B). Interestingly, a significant difference in the affinities of 21 and 30 for lectin AAL was observed ($EC_{50}$: 275 μM for 21 vs. 15 μM for 30), with the affinity of the core-fucosylated antibody being about 17 fold higher than that of core-fucosylated RNase B. To verify whether the observed difference majorly came from the difference in the nature of the N-glycans (core fucosylated high-mannose type in 21 vs. complex type in 30) or in the nature of proteins (the context of RNase vs. antibody), the N-glycans was released from the proteins by PNGase F treatment with in situ Fmoc labeling[71]. ELISA analysis of the AAL binding indicated that the affinity of the core-fucosylated complex type N-glycans ($EC_{50}$, 1.8 μM) released from antibody (30) was about 8 fold higher than that of the core-fucosylated high-mannose type N-glycans ($EC_{50}$, 16 μM) released from (21). Thus, the difference in AAL affinities between core-fucosylated RNase B (21) and core-fucosylated antibody (30) came mainly from the difference in the nature of the N-glycans (high mannose vs. complex type), and the protein part contributed to a less extent (ca. 2-fold).

The present invention establishes a highly efficient chemoenzymatic method for direct core-fucosylation of intact N-glycopeptides, N-glycoproteins, and therapeutic antibodies. This method was enabled by the discovery of an array of AlfC α-fucosidase mutants that act as novel glycoligases for transglycosylation using α-fucosyl fluoride as the simple donor substrates. The AlfC α-fucosidase mutants represent the first examples of glycoligases capable of specifically attaching an α1,6-fucose moiety to intact N-glycans of glycoproteins. The discovery of the α-fucoligases opens a new avenue to quickly constructing library of core-fucosylated N-glycopeptides and N-glycoproteins directly from the corresponding non-fucosylated counterparts, which have been hitherto difficult to obtain for glycomic studies.

Materials and Methods

All chemicals, reagents and solvents were purchased from Sigma-Aldrich and TCI, and unless specially noted, applied in the reaction without further purification. Monoclonal antibody rituximab was purchased from Premium Health Services Inc. (Columbia, Md.). Silica gel (200-425 mesh) for flash chromatography was purchased from Sigma-Aldrich. Analytical reverse-phase chromatography was performed on a Waters 626 HPLC instrument equipped with an)(Bridge BEH130 C18 column (3.5 μm, 4.6×250 mm) for reversed phase or YMC-Pack $NH_2$ column (5 μm, 4.6×250 mm) for normal phase. The XBridge column was eluted with a linear gradient of acetonitrile (0-30%, v/v) with water containing TFA (0.1%) over 35 min at a flowrate of 0.5 mL/min under UV 214 nm. The YMC-Pack NH$_2$ column was eluted with a linear gradient of ammonium formate (100 mM, pH4.5, 10-60%, v/v) with acetonitrile containing TFA (0.1%) over 80 min at a flowrate of 0.5 mL/min under UV 266 nm. Preparative HPLC was performed on a Waters 600 HPLC instrument equipped with a SymmetryPrep™ C18 column (7 μm, 19×300 mm). High-Performance Anion-Exchange Chromatography with Pulsed Amperometric Detection (HPAEC-PAD) was performed on a Dionex ICS-5000 chromatography system (Fischer Scientific) equipped with an electrochemical detector (ED$_{50}$) and an anion exchange column (CarboPac PA10 4×250 mm). The PA10 column was eluted with a constant buffer composed of 80% 100 mM NaOH and 20% water at a flowrate 1.0 mL/min. Liquid Chromatography Electrospray Mass spectrometry (LC-ESI-MS) was used to analyze transfer products including core fucosylated glycopeptides and glycoproteins. The LC-ESI-MS was performed on an Exactive™ Plus Orbitrap Mass Spectrometer (Thermo Scientific) equipped with a C18 column (proZap Expedite MS C18, 2.1×10 mm, 1.5 μm, P. J. Cobert Associates, Inc.) for glycopeptides, C8 column (Poroshell 300SB-C8, 1.0×75 mm, 5 μm, Agilent) for glycoproteins and C-4 column (XBridge™ BEH300 C4, 2.1×50 mm, 3.5 μm, Waters) for antibody analysis. $^1$H, $^{13}$C and $^1$H-$^1$H COS Y spectra were recorded on a 400 or 600 MHz spectrometer (Bruker, Tokyo, Japan) with D20 or DMSO-d$_6$ as the solvent. Amino acid sequence alignment for different fucosidases was performed using MAFFT, a multiple sequence alignment tool. Plasmid pCPD vector (CPD-Lasso) was created by engineering the CPD protein as a C-terminal tag into pET31(b) (Novagen) vector. PfuUltra II fusion HS DNA polymerase was purchased from Agilent. Restriction enzymes and *Escherichia coli* competent cells including 5-alpha and BL21 (DE3), used for DNA manipulation and protein production, were purchased from New England BioLabs Inc. Enzyme Kinetics was performed by GraFit (Erithacus Software, UK).

Construction, Expression and Purification of AlfC Fucosidase.

The DNA sequence encoded AlfC α1,6-fucosidase from *Lactobacillus casei* was synthesized (GenScript) and inserted into CPD-Lasso plasmid at NdeI and BamHI sites. The plasmid was transformed to BL21 (DE3) *E. coli* competent cell and AlfC α-fucosidases were overexpressed as CPD and 10×His tagged proteins in Luria-Bertani (1 L) broth with carbenicillin (0.1 mg/ml) at 37° C. for 4 h until the OD$_{600}$ up to 0.5. After induced by isopropyl β-D-1-thiogalactoside (0.2 mM) at 20° C. overnight, the cells were harvested by centrifugation at 8000 rpm and then disrupted by sonication. The supernatant of crude overexpressed enzyme was subjected to a Nickel-affinity chromatography in an AKTA prime plus system (GE Healthcare) equipped with a His-Trap column as previously described. The eluted target protein (69 kDa) was dialyzed against sodium phosphate (100 mM, pH7.4) and its concentration was determined by NanoDrop 2000c (Thermo Scientific).

Site-Directed Mutagenesis of AlfC α-Fucosidase.

The site-directed mutagenesis of AlfC α1,6-fucosidase was performed using Stratagene protocol. Two complementary primers (0.02 nmol) were employed in the polymerase chain reaction (PCR). After 14 cycles for PCR reaction, the reaction was mixed with DpnI (2,000 U/ml) and CutSmart buffer (1×), and incubated at 37° C. for 1 h. Then the plasmids in reaction mixture were transformed to NEB 5-alpha high efficiency competent cell for miniprep. After gene sequencing, the plasmid was transformed to BL21 (DE3) *E. coli* competent cell, following the same procedure of expression and purification described above. The purified AlfC mutants were characterized by SDS-PAGE. To remove the cysteine protease domain (CPD) tag, inositol hexaphosphate (10 mM) was mixed with AlfC mutants (1 mg) in PBS buffer (0.1 M, pH 7.0) at 4° C. overnight. The enzyme without CPD tag was then purified by Ni-NTA spin kit (QIAGEN). Purified AlfC mutants (44 kDa) were characterized by SDS-PAGE, compared with its counterpart with CPD tag.

Enzymatic Kinetics of Hydrolysis and Transfucosylation of AlfC and its Mutants.

Kinetic studies on the hydrolysis were carried out at 42° C. in sodium phosphate (0.1 M, pH 7.0). The amount of the released free fucose was detected by using Dionex chromatography. The concentration of the substrate 4-nitrophenyl α-fucoside (pNPFuc) was varied from 0.2 to 2.0 mM. $K_M$ and $k_{cat}$ values were determined by fitting the initial velocity curves to the Michaelis-Menten equation by nonlinear regression in GraFit (Erithacus Software).

The kinetic studies on transglycosylation were carried out at 42° C. in sodium phosphate (0.1 M, pH 7.5). The transglycosylation product was detected and quantitated by HPLC analysis. The concentration of the donor substrates (1-3) was varied from 0.2 to 2.0 mM, while that of the acceptor (4) was fixed (2 mM). $K_M$ and $k_{cat}$ values (strictly, apparent $K_M$ and $k_{cat}$, as they were determined at a fixed, nonsaturating, co-substrate concentration) were determined by fitting the initial velocity curves to the Michaelis-Menten equation by nonlinear regression in GraFit.

Fucosylation of 4.

To a mixture of 3 (0.249 mg, 1.5 μmol) and acceptor 4 (0.557 mg, 1 μmol) in a buffer (PBS, 100 mM, pH 7.5, 500 μL) containing 20% DMSO was added the E274A mutant (0.05 mg, 0.1 mg/mL), and the solution was incubated at 42° C. The reaction was monitored by LC-MS analysis on a C-18 column. After the reaction completed (30 min), the reaction mixture was quenched by 0.1% TFA, and then centrifuged and filtered through 0.45 μm syringe filter. The filtrate was concentrated and the residue was purified by reverse-phase (C18) HPLC to obtain the product (5) (0.63 mg, 99%) as a white powder after lyophilizaion. $^1$H NMR (DMSO-d$_6$+1% D$_2$O, 400 MHz): δ=7.88 (d, J=7.6 Hz, 2H, Ph-H), 7.71 (d, J=7.6 Hz, 2H, Ph-H), 7.41 (dd, J=7.6, 7.2 Hz, 2H, Ph-H), 7.32 (dd, J=7.2, 7.6 Hz, 2H, Ph-H), 4.80 (d, J$_{1,2}$=6.4 Hz, 1H, H-1), 4.62 (d, J$_{1,2}$=3.2 Hz, 1H, H-1'), 4.22 (m, 4H, Asn-H-2, Fmoc-H-2, Fmoc-H-1), 3.85 (m 1H, H-6), 3.77 (d, J=10 Hz, 1H, H-6), 3.50 (m, 3H, H-2', H-3', H-2), 3.46 (m, 1H, H-4'), 3.33 (m, 3H, H-3, H-4, H-5'), 3.09 (m, 1H, H-5), 2.54 (m, 2H, Asn-H-1), 1.78 (s, 3H, —COCH$_3$), 1.06 (d, J=6.8 Hz, 3H, —CH$_3$). $^{13}$C NMR (DMSO-d$_6$+1% D$_2$O, 100 MHz): δ=174.52 (C=O), 172.64 (C=O), 171.37 (C=O), 158.20 (C=O), 145.59 (Ph-C, 2C), 145.26 (Ph-C, 2C), 131.44 (Ph-C, 2C), 129.36 (Ph-C, 2C), 126.48 (Ph-C, 2C), 121.91 (Ph-C, 2C), 102.10 (C-1'), 88.62 (C-1), 77.03, 75.28, 72.77, 71.31, 70.85, 69.93, 68.48, 67.73, 67.02, 55.63, 51.85, 47.09, 36.52, 23.03 (COCH$_3$), 17.85 (C-6'). ESI-MS: calc. for 5, M=703.3 Da; found (m/z), 704.5 [M+H]$^+$, 726.6 [M+Na]$^+$. Analytical RP-HPLC, t$_R$=28.5 min.

Fucosylation of GlcNAc-Peptides. The Fucosylation of 6 as a Representative Procedure.

A mixture of 3 (0.249 mg, 1.5 μmol) and acceptor 6 (0.863 mg, 1 μmol) in a buffer (PBS, 100 mM, pH 7.5, 500 μL) containing the glycoligase mutant E274A (0.1 mg, 0.2 mg/mL) was incubated at 42° C. The reaction was monitored by LC-MS analysis. After the reaction was complete, the reaction mixture was quenched by 0.1% TFA, and then centrifuged and filtered through 0.45 μm syringe filter. The filtrate was dried, and the product was purified by RP-HPLC to give the fucosylated product (7) (1.00 mg, 99%). ESI-MS: Calcd. for 7, M=1008.6 Da; found (m/z), 505.43 $[M+2H]^{2+}$, 1009.68 $[M+H]^+$. Analytical RP-HPLC, $t_R$=6.5 min. the fucosylation of 8 and 10 followed the same procedure to give the fucosylated products 9 and 11 in almost quantitative yield.

Fucosylated Glycopeptide 9.

ESI-MS: Calcd. for 9, M=2197.0 Da; found (m/z), 550.79 $[M+4H]^{4+}$, 733.63 $[M+3H]^{3+}$, 1099.43 $[M+2H]^{2+}$. Analytical RP-HPLC, $t_R$=22.4 min.

Fucosylated Glycopeptide 9.

ESI-MS: calcd. for 11, M=4647.3 Da; found (m/z), 929.36 $[M+5H]^{5+}$, 1161.67 $[M+4H]^{4+}$, 1547.66 $[M+3H]^{3+}$. Analytical RP-HPLC, $t_R$=26.7 min.

Direct Core Fucosylation of Intact Glycopeptides. Fucosylation of 12 as a Representative Procedure.

To a mixture of 3 (0.249 mg, 1.5 μmol) and the acceptor (12) (2.86 mg, 1 μmol) in a buffer (PBS, 100 mM, pH7.5, 500 μL) was added mutant E274A (0.14 mg, 0.28 mg/mL). The solution was incubated at 42° C. The reaction was monitored by HPLC and LC-MS analysis. HPLC indicated the completion of the reaction after 45 min. Then the reaction was quenched with 0.1% TFA, and the mixture was centrifuged and filtered through 0.45 μm syringe filter. The filtrate was dried and the product was purified by RP-HPLC to give the fucosylated product (13) (2.81 mg, 93.4%). ESI-MS: calcd. for 13, M=3010.2 Da; found (m/z), 1004.73 $[M+3H]^{3+}$, 1506.68 $[M+2H]^{2+}$. Analytical RP-HPLC, $t_R$=4.2 min. The fucosylation of 14, 16, and 18 was performed in a similar manner and the reaction took 1-5 h to completion as monitored by HPLC analysis. The products were purified by RP-HPLC.

Fucosylated Glycopeptide 15 (92%).

ESI-MS: calcd. for 15, M=4198.2 Da; found (m/z), 840.60 $[M+5H]^{5+}$, 1050.48 $[M+4H]^{4+}$, 1400.72 $[M+3H]^{3+}$. Analytical RP-HPLC, $t_R$=16.0 min.

Fucosylated Glycopeptide 17 (91%).

ESI-MS: calcd. for 17, M=6641.7 Da; found (m/z), 1107.29 $[M+6H]^{6+}$, 1329.27 $[M+5H]^{5+}$, 1661.48 $[M+4H]^{4+}$. Analytical RP-HPLC, $t_R$=19.6 min.

Fucosylated Glycopeptide 19 (90%).

ESI-MS: calcd. for 19, M=6479.3 Da; found (m/z), 926.76 $[M+7H]^{7+}$, 1080.81 $[M+6H]^{6+}$, 1296.40 $[M+5H]^{5+}$, 1620.62 $[M+4H]^{4+}$. Analytical RP-HPLC, $t_R$=22.5 min.

Core Fucosylation of Ribonuclease B (20).

To a mixture of the α-fucosyl fluoride (3) (0.224 mg, 1.34 μmol) and the RNase B (20) (1.0 mg, 0.067 μmol) win the buffer (PBS, 100 mM, pH 7.5, 100 μL) was added mutant E274A (0.2 mg, 2 mg/mL). The solution was incubated at 37° C. The reaction was monitored by LC-MS analysis. After 5 h, the reaction was quenched by adding 0.1% TFA and the mixture was filtrated through a 0.45 μm syringe filter. The filtrate was subjected to RP-HPLC purification. The fractions containing the fucosylated (21) and afucosylated RNase B (20) were pooled and lyophilized. The residue was then dialyzed against sodium phosphate (100 mM, pH 7.4) at 4° C. Concentration of the RNase B mixture was determined by NanoDrop quantitation. ESI-MS: calcd. for 21, M=15042 Da (M5F), 15205 Da (M6F), 15368 Da (M7F), 15528 Da (M8F) and 15692 Da (M9F) Da; found (deconvolution data) (m/z): 15044 (M5F), 15207 (M6F), 15369 (M7F), 15530 (M8F) and 15693 (M9F). Analytical RP-HPLC, $t_R$=18.4 min.

To quantitate the M5-M9 glycan forms of RNase B, normal phase HPLC equipped with $NH_2$ column was used to separate and quantitate the fucosylated and afucosylated N-glycans after PNGase F releasing and labeling with Fmoc tag, as described below. The RNase B mixture (100 μg) was first denatured by treatment with 1 mL of guanidine hydrochloride (8 M) containing 1,4-dithiothreitol (180 mM). The mixture was incubated at 37° C. for 1 h. Then iodoacetamide (0.7 M) was added and the mixture was incubated at 37° C. for 1 h. The denatured RNase B mixture was dialyzed against sodium phosphate (100 mM, pH 8.5) at ambient temperature. To release and tag the N-glycans, the mixture was treated with PNGase F (10 U) (37° C. for 2 h). After that, 200 μL of Fmoc-Cl in acetone (50 mg/mL) was added and the mixture was incubated at 37° C. for 1 h. After centrifugation, the reaction mixture was washed with chloroform (3×200 μL) and the aqueous layer was passed through a Sep-Pak® C-18 cartridge to remove deglycosylated proteins. The purified Fmoc-labeling N-glycans was eluted and analyzed by normal HPLC. The ratios of each N-glycan form were calculated based on the peak integration. (MSF: 72%, M6F: 54%, M7F: 51%, M8F: 55% and M9F: 43%). NP-HPLC, $t_R$=39.8, 49.1, 56.9, 63.8 and 70.3 min, respectively.

Fucosylation of GlcNAc-Rituximab (27).

To a mixture of the α-fucosyl fluoride (3) (96 μg, 0.56 μmol) and the GlcNAc-rituximab (27) (2.0 mg, 0.014 μmol) in a buffer (PBS, 100 mM, pH 7.5, 100 μL) was added mutant E274A (200 μg, 2.0 mg/mL). The solution was incubated at 37° C. for 7 h, when LC-MS indicated complete conversion of 27 to the fully fucosylated product (29). The mixture was then loaded on a protein A affinity column (HiTrap Protein A HP, GE Healthcare). After washing, the desired product was eluted with citrate buffer (50 mM, pH 3.5) and promptly dialyzed against sodium phosphate (100 mM, pH 7.4) at 4° C. The solution was concentrated and the amount of fucosylated rituximab (29) was quantitated by NanoDrop analysis (1.80 mg, 90%). To verify the complete fucosylation at the Fc domain, the fucosylated rituximab (29) was treated with the IdeS protease (0.2 mg/mL) to release the monomeric Fc domain, which was then subjected to LC ESI-MS analysis. The ESI-MS revealed a single Fc species confirming the complete fucosylation of the Fc domain. ESI-MS: calcd. for the IdeS released Fc domain of 29, M=24108 Da; found (m/z), 965.53 $[M+25H]^{25+}$, 1005.36 $[M+24H]^{24+}$, 1049.23 $[M+23H]^{23+}$, 1096.91 $[M+22H]^{22+}$, 1149.06 $[M+21H]^{21+}$, 1206.02 $[M+20H]^{20+}$, 1269.72 $[M+19H]^{19+}$, 1340.18 $[M+18H]^{18+}$, and 1419.02 $[M+17H]^{17+}$; Deconvolution of the ESI-MS, M=24110 Da.

Fucosylation of Intact Rituximab (28) and ESI-MS Analysis of the Fucosylated Intact Antibody (30).

To a mixture of the α-fucosyl fluoride (3) (46.3 μg, 0.27 μmol) and the intact rituximab (28) (1.0 mg, 0.0067 μmol) in a buffer (PBS, 100 mM, pH 7.5, 100 μL) was added mutant E274A (200 μg, 2.0 mg/mL). The fucosylation of 28 was performed in a similar manner with that of 27 and the reaction took 8 h to completion as monitored by LC-MS analysis. The products were purified by protein A affinity column and was quantitated by NanoDrop analysis (0.87 mg, 87%). The ESI-MS revealed a single species confirming the complete fucosylation in the intact rituximab (30). ESI-MS: calcd. for 30, M=148888 Da; found (m/z), 2708.01 $[M+55H]^{55+}$, 2758.17 $[M+54H]^{54+}$, 2810.16 $[M+53H]^{53+}$, 2864.21 $[M+52H]^{52+}$, 2920.29 $[M+51H]^{51+}$, 2978.64 $[M+50H]^{50+}$, 3039.40 $[M+49H]^{49+}$, 3102.70 $[M+48H]^{48+}$, 3168.70 $[M+47H]^{47+}$; Deconvolution of the ESI-MS, M=148886 Da.

Lectin Binding Studies of the Core-Fucosylated RNase B and Rituximab.

The glycoprotein (20, 21, 28 or 30) (10 µg/ml) in a phosphate buffer (pH 7.5) was coated onto a 96-well plate (UltraCruz®) at 4° C. for overnight. After wash twice, 2% bovine serum albumin in PBS containing Tween® 20 (PBST buffer) was added to block the plate for 2 h. Subsequently, after washed twice again, a serial dilution of AAL-biotin ranging from 0.1 µM to 1000 µM in PBST buffer was added and the plate was incubated for 1 h. After washing, peroxidase streptavidin (2 µg/mL) (Jackson ImmunoResearch Inc.) was added and incubated for 1 h. Finally, 100 µL of substrate, 3, 3', 5, 5'-tetramethylbenzidine was added for signal development. The reaction was stopped by the adding 100 µL of 20% sulfuric acid (v/v). The absorbance at 450 nm was measured using SpectraMax M5 microplate reader (Molecular Devices). For the binding of the N-glycans, the Fmoc-labeled N-glycans released from 20, 21, 28 and 30 (1 µg/ml) were coated on the plate and the ELISA analysis was performed in the same manner as that of the glycoproteins.

REFERENCES

The contents of the following references cited herein are incorporated by reference herein for all purposes.
(1) Dwek, R. A. *Chem. Rev.* 1996, 96, 683.
(2) Helenius, A.; Aebi, M. *Science* 2001, 291, 2364.
(3) Petrescu, A. J.; Wormald, M. R.; Dwek, R. A. *Curr. Opin. Struct. Biol.* 2006, 16, 600.
(4) Varki, A. *Glycobiology* 1993, 3, 97.
(5) Haltiwanger, R. S.; Lowe, J. B. *Annu. Rev. Biochem.* 2004, 73, 491.
(6) Dube, D. H.; Bertozzi, C. R. *Nat. Rev. Drug Discov.* 2005, 4, 477.
(7) Nimmerjahn, F.; Ravetch, J. V. *Nat. Rev. Immunol.* 2008, 8, 34.
(8) Jefferis, R. *Nat. Rev. Drug Discov.* 2009, 8, 226.
(9) Hart, G. W.; Copeland, R. J. *Cell* 2010, 143, 672.
(10) Taniguchi, N.; Kizuka, Y. *Adv. Cancer Res.* 2015, 126, 11.
(11) Pinho, S. S.; Reis, C. A. *Nat. Rev. Cancer* 2015, 15, 540.
(12) Chen, C. Y.; Jan, Y H.; Juan, Y H.; Yang, C. J.; Huang, M. S.; Yu, C. J.; Yang, P. C.; Hsiao, M.; Hsu, T. L.; Wong, C. H. *Proc. Natl. Acad. Sci. USA* 2013, 110, 630.
(13) Sato, Y; Nakata, K.; Kato, Y; Shima, M.; Ishii, N.; Koji, T.; Taketa, K.; Endo, Y.; Nagataki, S. *N. Engl. J. Med.* 1993, 328, 1802.
(14) Wang, X.; Inoue, S.; Gu, J.; Miyoshi, E.; Noda, K.; Li, W.; Mizuno-Horikawa, Y.; Nakano, M.; Asahi, M.; Takahashi, M.; Uozumi, N.; Ihara, S.; Lee, S. H.; Ikeda, Y.; Yamaguchi, Y.; Aze, Y; Tomiyama, Y.; Fujii, J.; Suzuki, K.; Kondo, A.; Shapiro, S. D.; Lopez-Otin, C.; Kuwaki, T.; Okabe, M.; Honke, K.; Taniguchi, N. *Proc. Natl. Acad. Sci. USA* 2005, 102, 15791.
(15) Mimura, Y; Katoh, T.; Saldova, R.; O'Flaherty, R.; Izumi, T.; Mimura-Kimura, Y.; Utsunomiya, T.; Mizukami, Y.; Yamamoto, K.; Matsumoto, T.; Rudd, P. M. *Protein Cell* 2017.
(16) Lee, S. H.; Takahashi, M.; Honke, K.; Miyoshi, E.; Osumi, D.; Sakiyama, H.; Ekuni, A.; Wang, X.; Inoue, S.; Gu, J.; Kadomatsu, K.; Taniguchi, N. *J. Biochem.* 2006, 139, 391.
(17) Wang, X.; Gu, J.; Ihara, H.; Miyoshi, E.; Honke, K.; Taniguchi, N. *J. Biol. Chem.* 2006, 281, 2572.
(18) Pinho, S. S.; Seruca, R.; Gartner, F.; Yamaguchi, Y.; Gu, J.; Taniguchi, N.; Reis, C. A. *Cell. Mol. Life Sci.* 2011, 68, 1011.
(19) Lin, H.; Wang, D.; Wu, T.; Dong, C.; Shen, N.; Sun, Y.; Xie, H.; Wang, N.; Shan, L. *Am. J. Physiol. Renal. Physiol.* 2011, 300, F1017.
(20) Venkatachalam, M. A.; Weinberg, J. M. *Kidney Int.* 2013, 84, 11.
(21) Li, W.; Yu, R.; Ma, B.; Yang, Y.; Jiao, X.; Liu, Y; Cao, H.; Dong, W.; Liu, L.; Ma, K.; Fukuda, T.; Liu, Q.; Ma, T.; Wang, Z.; Gu, J.; Zhang, J.; Taniguchi, N. *J. Immunol.* 2015, 194, 2596.
(22) Andre, S.; Kozar, T.; Kojima, S.; Unverzagt, C.; Gabius, H. *J. Biol. Chem.* 2009, 390, 557.
(23) Andre, S.; Kozar, T.; Schuberth, R.; Unverzagt, C.; Kojima, S.; Gabius, H. *J. Biochemistry* 2007, 46, 6984.
(24) Schmaltz, R. M.; Hanson, S. R.; Wong, C. H. *Chem. Rev.* 2011, 111, 4259.
(25) Rillahan, C. D.; Paulson, J. C. *Annu. Rev. Biochem.* 2011, 80, 797.
(26) Kiessling, L. L.; Splain, R. A. *Annu. Rev. Biochem.* 2010, 79, 619.
(27) Voynow, J. A.; Kaiser, R. S.; Scanlin, T. F.; Glick, M. C. *J. Biol. Chem.* 1991, 266, 21572.
(28) Yang, Q.; Wang, L. X. *J. Biol. Chem.* 2016, 291, 11064.
(29) Li, L.; Liu, Y.; Ma, C.; Qu, J.; Calderon, A. D.; Wu, B.; Wei, N.; Wang, X.; Guo, Y; Xiao, Z.; Song, J.; Sugiarto, G.; Li, Y.; Yu, H.; Chen, X.; Wang, P. G. *Chem. Sci.* 2015, 6, 5652.
(30) Brzezicka, K.; Echeverria, B.; Serna, S.; van Diepen, A.; Hokke, C. H.; Reichardt, N. C. *ACS Chem. Biol.* 2015, 10, 1290.
(31) Calderon, A. D.; Liu, Y.; Li, X.; Wang, X.; Chen, X.; Li, L.; Wang, P. G. *Org. Biomol. Chem.* 2016, 14, 4027.
(32) Tseng, T. H.; Lin, T. W.; Chen, C. Y.; Chen, C. H.; Lin, J. L.; Hsu, T. L.; Wong, C. H. *J. Am. Chem. Soc.* 2017, 139, 9431.
(33) Yang, Q.; Zhang, R.; Cai, H.; Wang, L. X. *J. Biol. Chem.* 2017, July 20. pii: jbc.M117.804070. doi: 10.1074/jbc.M117.804070. [Epub ahead of print].
(34) Nagorny, P.; Fasching, B.; Li, X.; Chen, G.; Aussedat, B.; Danishefsky, S. J. *J. Am. Chem. Soc.* 2009, 131, 5792.
(35) Sun, B.; Srinivasan, B.; Huang, X. *Chem. Eur. J.* 2008, 14, 7072.
(36) MacKenzie, L. F.; Wang, Q.; Warren, R. A. J.; Withers, S. G. *J. Am. Chem. Soc.* 1998, 120, 5583.
(37) Moracci, M.; Trincone, A.; Perugino, G.; Ciaramella, M.; Rossi, M. *Biochemistry* 1998, 37, 17262.
(38) Malet, C.; Planas, A. *FEBS Lett.* 1998, 440, 208.
(39) Perugino, G.; Trincone, A.; Rossi, M.; Moracci, M. *Trends Biotechnol.* 2004, 22, 31.
(40) Hancock, S. M.; Vaughan, M. D.; Withers, S. G. *Curr. Opin. Chem. Biol.* 2006, 10, 509.
(41) Shaikh, F. A.; Withers, S. G. *Biochem. Cell Biol.* 2008, 86, 169.
(42) Cobucci-Ponzano, B.; Moracci, M. *Nat. Prod. Rep.* 2012, 29, 697.
(43) Wang, L. X.; Amin, M. N. *Chem. Biol.* 2014, 21, 51.
(44) Jahn, M.; Marles, J.; Warren, R. A.; Withers, S. G. *Angew. Chem. Int. Ed.* 2003, 42, 352.
(45) Kim, Y. W.; Zhang, R.; Chen, H.; Withers, S. G. *Chem. Commun. (Camb)* 2010, 46, 8725.
(46) Li, C.; Ahn, H. J.; Kim, J. H.; Kim, Y W. *Carbohydr. Polym.* 2014, 99, 39.
(47) Danby, P. M.; Withers, S. G. *ACS Chem. Biol.* 2016, 11, 1784.
(48) Sakurama, H.; Fushinobu, S.; Hidaka, M.; Yoshida, E.; Honda, Y.; Ashida, H.; Kitaoka, M.; Kumagai, H.; Yamamoto, K.; Katayama, T. *J. Biol. Chem.* 2012, 287, 16709.

(49) Wada, J.; Honda, Y.; Nagae, M.; Kato, R.; Wakatsuki, S.; Katayama, T.; Taniguchi, H.; Kumagai, H.; Kitaoka, M.; Yamamoto, K. *FEBS Lett.* 2008, 582, 3739.
(50) Sugiyama, Y.; Gotoh, A.; Katoh, T.; Honda, Y; Yoshida, E.; Kurihara, S.; Ashida, H.; Kumagai, H.; Yamamoto, K.; Kitaoka, M.; Katayama, T. *Glycobiology* 2016, 26, 1235.
(51) Sugiyama, Y; Katoh, T.; Honda, Y; Gotoh, A.; Ashida, H.; Kurihara, S.; Yamamoto, K.; Katayama, T. *Biosci. Biotechnol. Biochem.* 2017, 81, 283.
(52) Cobucci-Ponzano, B.; Conte, F.; Bedini, E.; Corsaro, M. M.; Parrilli, M.; Sulzenbacher, G.; Lipski, A.; Dal Piaz, F.; Lepore, L.; Rossi, M.; Moracci, M. *Chem. Biol.* 2009, 16, 1097.
(53) Cobucci-Ponzano, B.; Zorzetti, C.; Strazzulli, A.; Bedini, E.; Corsaro, M. M.; Sulzenbacher, G.; Rossi, M.; Moracci, M. *Biocatalysis and Biotransformation* 2012, 30, 288.
(54) Cobucci-Ponzano, B.; Zorzetti, C.; Strazzulli, A.; Carillo, S.; Bedini, E.; Corsaro, M. M.; Comfort, D. A.; Kelly, R. M.; Rossi, M.; Moracci, M. *Glycobiology* 2011, 21, 448.
(55) Rodriguez-Diaz, J.; Monedero, V.; Yebra, M. J. *Appl. Environ. Microbiol.* 2011, 77, 703.
(56) Rodriguez-Diaz, J.; Carbajo, R. J.; Pineda-Lucena, A.; Monedero, V.; Yebra, M. J. *Appl. Environ. Microbiol.* 2013, 79, 3847.
(57) Becerra, J. E.; Coll-Marques, J. M.; Rodriguez-Diaz, J.; Monedero, V; Yebra, M. J. *Appl. Microbiol. Biotechnol.* 2015, 99, 7165.
(58) Ashida, H.; Miyake, A.; Kiyohara, M.; Wada, J.; Yoshida, E.; Kumagai, H.; Katayama, T.; Yamamoto, K. *Glycobiology* 2009, 19, 1010.
(59) Sakurama, H.; Tsutsumi, E.; Ashida, H.; Katayama, T.; Yamamoto, K.; Kumagai, H. *Biosci. Biotechnol. Biochem.* 2012, 76, 1022.
(60) Sulzenbacher, G.; Bignon, C.; Nishimura, T.; Tarling, C. A.; Withers, S. G.; Henrissat, B.; Bourne, Y *J. Biol. Chem.* 2004, 279, 13119.
(61) Liu, S. W.; Chen, C. S.; Chang, S. S.; Mong, K. K.; Lin, C. H.; Chang, C. W.; Tang, C. Y; Li, Y K. *Biochemistry* 2009, 48, 110.
(62) Shaikh, F. A.; Lammerts van Bueren, A.; Davies, G. J.; Withers, S. G. *Biochemistry* 2013, 52, 5857.
(63) Shen, A.; Lupardus, P. J.; Morell, M.; Ponder, E. L.; Sadaghiani, A. M.; Garcia, K. C.; Bogyo, M. *PloS One* 2009, 4, e8119.
(64) Lomino, J. V; Tripathy, A.; Redinbo, M. R. *J. Bacteriol.* 2011, 193, 2089.
(65) Li, T.; Tong, X.; Yang, Q.; Giddens, J. P.; Wang, L. X. *J. Biol. Chem.* 2016, 291, 16508.
(66) Giddens, J. P.; Lomino, J. V; Amin, M. N.; Wang, L. X. *J. Biol. Chem.* 2016, 291, 9356.
(67) Wang, L. X. *Chem. Biol.* 2009, 16, 1026.
(68) Williams, S. J.; Withers, S. G. *Carbohydr. Res.* 2000, 327, 27.
(69) Huang, W.; Li, J.; Wang, L. X. *Chem Bio Chem* 2011, 12, 932.
(70) Wang, L. X.; Song, H.; Liu, S.; Lu, H.; Jiang, S.; Ni, J.; Li, H. *Chem Bio Chem* 2005, 6, 1068.
(71) Kamoda, S.; Nakano, M.; Ishikawa, R.; Suzuki, S.; Kakehi, K. *J. Proteome Res.* 2005, 4, 146.
(72) Amin, M. N.; Huang, W.; Mizanur, R. M.; Wang, L. X. *J. Am. Chem. Soc.* 2011, 133, 14404.
(73) Huang, W.; Yang, Q.; Umekawa, M.; Yamamoto, K.; Wang, L. X. *Chem Bio Chem* 2010, 11, 1350.
(74) Li, T.; DiLillo, D. J.; Bournazos, S.; Giddens, J. P.; Ravetch, J. V.; Wang, L. X. *Proc. Natl. Acad. Sci. USA* 2017, 114, 3485.
(75) Huang, W.; Giddens, J.; Fan, S. Q.; Toonstra, C.; Wang, L. X. *J. Am. Chem. Soc.* 2012, 134, 12308.
(76) Nakano, M.; Nakagawa, T.; Ito, T.; Kitada, T.; Hijioka, T.; Kasahara, A.; Tajiri, M.; Wada, Y.; Taniguchi, N.; Miyoshi, E. *Int. J. Cancer* 2008, 122, 2301.
(77) Lai, J. I.; Licht, A. F.; Dugast, A. S.; Suscovich, T.; Choi, I.; Bailey-Kellogg, C.; Alter, G.; Ackerman, M. E. *J. Virol.* 2014, 88, 2799.

TABLE 1

Complementary primer pair of each AlfC mutant. The underline indicates the mutation for each mutant

| AlfC mutants | Primer pair | |
|---|---|---|
| D200A | Fw: CGCGACCGCCTGGTTCGCCGTGCCGATGACGCTGT | (SEQ ID NO: 14) |
| | Rv: ACAGCGTCATCGGCACGGCGAACCAGGCGGTCGCG | (SEQ ID NO: 15) |
| D200S | Fw: CGCGACCGCCTGGTTCTCCGTGCCGATGACGCTGT | (SEQ ID NO: 16) |
| | Rv: ACAGCGTCATCGGCACGGAGAACCAGGCGGTCGCG | (SEQ ID NO: 17) |
| D200G | Fw: CGCGACCGCCTGGTTCGGCGTGCCGATGACGCTGT | (SEQ ID NO: 18) |
| | Rv: ACAGCGTCATCGGCACGCCGAACCAGGCGGTCGCG | (SEQ ID NO: 19) |
| D200T | Fw: CGCGACCGCCTGGTTCACCGTGCCGATGACGCTGT | (SEQ ID NO: 20) |
| | Rv: ACAGCGTCATCGGCACGGTGAACCAGGCGGTCGCG | (SEQ ID NO: 21) |
| E274A | Fw: CACCGCTGGGTCTGTACGCAACCGCGGGCACGATTAA | (SEQ ID NO: 22) |
| | Rv: TTAATCGTGCCCGCGGTTGCGTACAGACCCAGCGGTG | (SEQ ID NO: 23) |
| E274S | Fw: CACCGCTGGGTCTGTACTCAACCGCGGGCACGATTAA | (SEQ ID NO: 24) |
| | Rv: TTAATCGTGCCCGCGGTTGAGTACAGACCCAGCGGTG | (SEQ ID NO: 25) |
| E274G | Fw: CACCGCTGGGTCTGTACGGAACCGCGGGCACGATTAA | (SEQ ID NO: 26) |
| | Rv: TTAATCGTGCCCGCGGTTCCGTACAGACCCAGCGGTG | (SEQ ID NO: 27) |
| E274D | Fw: CCGCTGGGTCTGTACGATACCGCGGGCACG | (SEQ ID NO: 28) |
| | Rv: CGTGCCCGCGGTATCGTACAGACCCAGCGG | (SEQ ID NO: 29) |

TABLE 2

Transglycosylation kinetics of AlfC α-fucosidase mutants.[a]

| Enzyme | $k_{cat}$ (min$^{-1}$) | $K_M$ (mM) | $k_{cat}/K_M$ (min$^{-1}$mM$^{-1}$) |
|---|---|---|---|
| E274G (a/b)[b] | $1.38 \pm 0.15 \times 10^2$ | $0.25 \pm 0.03$ | $5.52 \pm 0.41 \times 10^2$ |
| E274A (a/b)[b] | $2.73 \pm 0.18 \times 10^2$ | $0.17 \pm 0.02$ | $16.1 \pm 0.89 \times 10^2$ |
| E274S (a/b)[b] | $2.42 \pm 0.14 \times 10^2$ | $0.26 \pm 0.03$ | $9.31 \pm 0.56 \times 10^2$ |

[a] Conditions: Donor sugar (0.2 to 2.0 mM), acceptor (2.0 mM), sodium phosphate (0.1M, pH 7.5), 42° C.

That which is claimed is:

1. A mutated α1-6-fucosidase enzyme selected from the group consisting of E274A (SEQ ID NO: 1), E274S (SEQ ID NO: 2), and E274G (SEQ ID NO: 3).

2. A kit comprising a least one *Lactobacillus casei* α-fucosidase mutant selected from the group consisting of E274A (SEQ ID NO: 1), E274S (SEQ ID NO: 2), and E274G (SEQ ID NO: 3).

3. A catalytic method for fucosylating a N-glycopeptide or N-glycoprotein, the method comprising:
   providing a GlcNAc acceptor substrate comprising a GlcNAc containing peptide or protein, or an oligosaccharide containing a terminal GlcNAc moiety;
   providing an activated glycosyl donor for access to a sugar fucose; and
   providing an α1,6-fucosidase mutant enzyme for enzymatically transfucosylating the GlcNAc acceptor substrate with the sugar fucose,
   wherein the α1,6-fucosidase mutant enzyme is a *Lactobacillus casei* α1,6-fucosidase mutant, thereby synthesizing a fucosylated glycopeptide or glycoprotein, wherein α1,6-fucosidase mutant enzyme is selected from a group consisting of E274A (SEQ ID NO: 1), E274S (SEQ ID NO: 2), and E274G (SEQ ID NO:3) derived from *Lactobacillus casei* α-fucosidase (SEQ ID NO: 4).

4. The catalytic method according to claim 3, wherein the activated glycosyl donor is selected from the group consisting of α-fucosyl fluoride αFucF, α-fucosyl chloride, α-fucosyl azide, 4-nitrophenyl α-fucoside, 3-nitrophenyl α-fucoside, 3,4-dinitrophenyl α-fucoside, and 4-methylumbelliferyl α-fucoside.

5. The catalytic method according to claim 3, further comprising a cysteine protease domain (CPD) and poly histidine (HIS) (SEQ ID NO: 31) or a CPD (SEQ ID NO: 30) polypeptide.

6. A chemoenzymatic method for the preparation of homogeneous fucosylated glycopeptides or glycoproteins, comprising:
   providing a nonfucosylated glycopeptide or glycoprotein acceptor; and
   reacting the nonfucosylated glycopeptide or glycoprotein acceptor with a donor substrate including an activated fucose containing moiety, in the presence of a *Lactobacillus casei* α1-6-fucosidase E274 mutant protein or fragment thereof comprising a catalytic domain having a E274 mutation and exhibits increased transfucosylation and reduced hydrolytic activity relative to the wild type α1-6-fucosidase E274 enzyme (SEQ ID NO: 4) to transfer the activated fucose containing moiety to the nonfucosylated glycopeptide or glycoprotein acceptor and yielding the homogeneous fucosylated glycopeptides or glycoproteins, wherein α1,6-fucosidase mutant enzyme is selected from a group consisting of E274A (SEQ ID NO: 1), E274S (SEQ ID NO: 2), and E274G (SEQ ID NO:3).

7. The chemoenzymatic method according to claim 6, wherein the homogeneous fucosylated glycopeptides and glycoproteins include glycans attached to the glycopeptides or glycoproteins selected from high mannose type, sialylated and asialo-complex type, hybrid type and their analogs.

8. The chemoenzymatic method according to claim 6, wherein the nonfucosylated glycopeptide or glycoprotein acceptor include one or more Asn(asparagine)-linked GlcNAc moieties or one or more N-glycan sites to allow introduction of one or multiple core fucoses.

9. The chemoenzymatic method according to claim 6, wherein the fucosylated glycopeptides or glycoproteins is an antibody, wherein the antibody is selected from a group consisting of 17b, 48d, A32, C11, 2G12, F240, IgG1b12, 19e, X5, TNX-355, cetuximab, rituximab, muromonab-CD3, abciximab, daclizumab, basiliximab, palivizumab, infliximab, trastuzumab, gemtuzumab ozogamicin, alemtuzumab, ibritumomab tiuxetan, adalimumab, omalizumab, tositumomab, I131 tositumomab, efalizumab, bevacizumab, panitumumab, pertuzumab, natalizumab, etanercept, IGN101, volociximab, Anti-CD80 mAb, Anti-CD23 mAb, CAT-3888, CDP-791, MDX-010, MDX-060, MDX-070, matuzumab, CP-675,206, CAL, SGN-30, zanolimumab, adecatumumab, oregovomab, nimotuzumab, ABT-874, denosumab, AM 108, AMG 714, fontolizumab, daclizumab, golimumab, CNTO 1275, ocrelizumab, HuMax-CD20, belimumab, epratuzumab, MLN1202, visilizumab, tocilizumab, certolizumab pegol, eculizumab, pexelizumab, abciximab, ranbizumab, mepolizumab and MYO-029.

10. The chemoenzymatic method according to claim 6, wherein the activated fucose containing moiety is selected from the group consisting of α-fucosyl fluoride αFucF, α-fucosyl chloride, α-fucosyl azide, 4-nitrophenyl α-fucoside, 3-nitrophenyl α-fucoside, 3,4-dinitrophenyl α-fucoside, and 4-methylumbelliferyl α-fucoside.

11. The chemoenzymatic method according to claim 6, further comprising a cysteine protease domain (CPD) and HIS (SEQ ID NO: 31) or a CPD (SEQ ID NO: 30) polypeptide.

* * * * *